(12) United States Patent
Schoonmaker et al.

(10) Patent No.: US 10,188,804 B2
(45) Date of Patent: *Jan. 29, 2019

(54) CONTACT TRIGGER RELEASE NEEDLE GUARD

(71) Applicant: Safety Syringes, Inc., Franklin Lakes, NJ (US)

(72) Inventors: Ryan Schoonmaker, San Marcos, CA (US); Dustin Hahn, Carlsbad, CA (US)

(73) Assignee: Safety Syringes, Inc., Franklin Lakes, NJ (US)

(*) Notice: Subject to any disclaimer, the term of this patent is extended or adjusted under 35 U.S.C. 154(b) by 59 days.

This patent is subject to a terminal disclaimer.

(21) Appl. No.: 15/377,232

(22) Filed: Dec. 13, 2016

(65) Prior Publication Data

US 2017/0087308 A1    Mar. 30, 2017

Related U.S. Application Data

(62) Division of application No. 13/671,309, filed on Nov. 7, 2012, now Pat. No. 9,579,468.

(60) Provisional application No. 61/556,674, filed on Nov. 7, 2011.

(51) Int. Cl.
*A61M 5/32* (2006.01)

(52) U.S. Cl.
CPC ........ *A61M 5/3257* (2013.01); *A61M 5/3213* (2013.01); *A61M 2005/3261* (2013.01); *A61M 2205/581* (2013.01); *A61M 2205/582* (2013.01)

(58) Field of Classification Search
CPC .............. A61M 5/3257; A61M 5/3213; A61M 2205/581; A61M 2205/582; A61M 2005/3261

See application file for complete search history.

(56) References Cited

U.S. PATENT DOCUMENTS

| 2,876,770 | A | 3/1959 | White |
| 4,664,654 | A | 5/1987 | Strauss |
| 4,725,267 | A | 2/1988 | Vaillancourt |
| 4,795,432 | A | 1/1989 | Karczmer |
| 4,804,371 | A | 2/1989 | Vaillancourt |
| 4,850,977 | A | 7/1989 | Bayless |

(Continued)

FOREIGN PATENT DOCUMENTS

| EP | 0268445 B1 | 1/1991 |
| EP | 0763369 A1 | 3/1997 |

(Continued)

*Primary Examiner* — Amber Stiles
(74) *Attorney, Agent, or Firm* — The Webb Law Firm

(57) ABSTRACT

A needle guard device mountable to a pre-filled syringe in its ready-to-fill state. The device includes a lock collar and a device shield biased to move relative to the lock collar. The lock collar interfaces with the syringe neck to attach the device to the syringe. With the removal of a needle shield assembly comprising rigid and soft needle shields, the lock collar and device shield are free to move proximally along the syringe neck and interact with a syringe step down area to activate the device. As the device moves proximally, retention arms of the device shield interact with the syringe step down, causing the arms to deflect radially outwards to disengage from the lock collar triggering the device shield to move from a first position to a second position.

19 Claims, 27 Drawing Sheets

(56) References Cited

U.S. PATENT DOCUMENTS

| | | |
|---|---|---|
| 4,887,998 A | 12/1989 | Martin et al. |
| 4,894,055 A | 1/1990 | Sudnak |
| 4,911,693 A | 3/1990 | Paris |
| 4,932,940 A | 6/1990 | Walker et al. |
| 5,104,384 A | 4/1992 | Parry |
| 5,104,385 A | 4/1992 | Huband |
| 5,135,510 A | 8/1992 | Maszkiewicz et al. |
| 5,242,401 A | 9/1993 | Colsky |
| 5,267,977 A | 12/1993 | Feeney, Jr. |
| 5,292,314 A | 3/1994 | D'Alessio et al. |
| 5,295,975 A | 3/1994 | Lockwood, Jr. |
| 5,300,045 A | 4/1994 | Plassche, Jr. |
| 5,348,544 A | 9/1994 | Sweeney et al. |
| 5,360,408 A | 11/1994 | Vaillancourt |
| 5,360,409 A | 11/1994 | Boyd, III et al. |
| 5,368,568 A | 11/1994 | Pitts et al. |
| 5,383,857 A | 1/1995 | Levitov |
| 5,385,557 A | 1/1995 | Thompson |
| 5,389,085 A | 2/1995 | D'Alessio et al. |
| 5,403,286 A | 4/1995 | Lockwood, Jr. |
| 5,405,330 A | 4/1995 | Zunitch et al. |
| 5,411,487 A | 5/1995 | Castagna |
| 5,417,660 A | 5/1995 | Martin |
| 5,423,758 A | 6/1995 | Shaw |
| 5,423,766 A | 6/1995 | Di Cesare |
| 5,429,612 A | 7/1995 | Berthier |
| 5,433,712 A | 7/1995 | Stiles et al. |
| 5,437,647 A | 8/1995 | Firth et al. |
| 5,466,223 A | 11/1995 | Bressler et al. |
| 5,478,316 A | 12/1995 | Bitdinger et al. |
| 5,486,163 A | 1/1996 | Haynes |
| 5,503,627 A | 4/1996 | McKinnon et al. |
| 5,512,050 A | 4/1996 | Caizza et al. |
| 5,527,294 A | 6/1996 | Weatherford et al. |
| 5,549,558 A | 8/1996 | Martin |
| 5,554,129 A | 9/1996 | Stevenson |
| 5,558,651 A | 9/1996 | Crawford et al. |
| 5,562,626 A | 10/1996 | Sanpietro |
| 5,573,513 A | 11/1996 | Wozencroft |
| 5,582,598 A | 12/1996 | Chanoch |
| 5,584,810 A | 12/1996 | Brimhall |
| 5,591,138 A | 1/1997 | Vaillancourt |
| 5,599,313 A | 2/1997 | Gyure et al. |
| 5,601,535 A | 2/1997 | Byrne et al. |
| 5,609,577 A | 3/1997 | Haber et al. |
| 5,656,031 A | 8/1997 | Thorne et al. |
| 5,658,256 A | 8/1997 | Shields |
| 5,669,888 A | 9/1997 | Trapp |
| 5,672,883 A | 9/1997 | Reich |
| 5,685,863 A | 11/1997 | Botich et al. |
| 5,688,241 A | 11/1997 | Asbaghi |
| 5,695,475 A | 12/1997 | Best, Jr. et al. |
| 5,709,668 A | 1/1998 | Wacks |
| 5,733,265 A | 3/1998 | Bachman et al. |
| 5,746,215 A | 5/1998 | Manjarrez |
| 5,746,727 A | 5/1998 | Graves et al. |
| 5,795,336 A | 8/1998 | Romano et al. |
| 5,800,395 A | 9/1998 | Botich et al. |
| 5,810,775 A | 9/1998 | Shaw |
| 5,879,338 A | 3/1999 | Mahurkar |
| 5,893,845 A | 4/1999 | Newby et al. |
| 5,910,130 A | 6/1999 | Caizza et al. |
| 5,919,168 A | 7/1999 | Wheeler |
| 5,925,020 A | 7/1999 | Nestell |
| 5,961,491 A | 10/1999 | McGary et al. |
| 5,976,111 A | 11/1999 | Hart |
| 5,984,899 A | 11/1999 | D'Alessio et al. |
| 6,017,329 A | 1/2000 | Hake |
| 6,086,563 A | 7/2000 | Moulton et al. |
| 6,086,568 A | 7/2000 | Caizza |
| 6,099,500 A | 8/2000 | Dysarz |
| 6,162,197 A | 12/2000 | Mohammad |
| 6,179,812 B1 | 1/2001 | Botich et al. |
| 6,193,695 B1 | 2/2001 | Rippstein, Jr. |
| 6,197,007 B1 | 3/2001 | Thorne et al. |
| 6,203,529 B1 | 3/2001 | Gabriel et al. |
| 6,210,371 B1 | 4/2001 | Shaw |
| 6,213,987 B1 | 4/2001 | Hirsch et al. |
| 6,221,052 B1 | 4/2001 | Caizza et al. |
| 6,261,265 B1 | 7/2001 | Mosseri |
| 6,293,925 B1 | 9/2001 | Safabash et al. |
| 6,309,375 B1 | 10/2001 | Glines et al. |
| 6,315,113 B1 | 11/2001 | Britton et al. |
| 6,319,233 B1 | 11/2001 | Jansen et al. |
| 6,379,336 B1 | 4/2002 | Asbaghi et al. |
| 6,409,706 B1 | 6/2002 | Loy |
| 6,413,236 B1 | 7/2002 | Van Dyke |
| 6,458,105 B1 | 10/2002 | Rippstein, Jr. et al. |
| 6,461,362 B1 | 10/2002 | Halseth et al. |
| 6,471,677 B2 | 10/2002 | Domici, Jr. |
| 6,475,191 B2 | 11/2002 | Tamura et al. |
| 6,475,194 B2 | 11/2002 | Domici, Jr. et al. |
| 6,517,516 B1 | 2/2003 | Caizza |
| 6,524,278 B1 | 2/2003 | Campbell et al. |
| 6,527,742 B1 | 3/2003 | Malenchek |
| 6,530,904 B1 | 3/2003 | Edwards et al. |
| 6,547,762 B1 | 4/2003 | Botich et al. |
| 6,547,764 B2 | 4/2003 | Larsen et al. |
| 6,565,540 B1 | 5/2003 | Perouse et al. |
| 6,575,939 B1 | 6/2003 | Brunel |
| 6,589,158 B2 | 7/2003 | Winkler |
| 6,605,073 B1 | 8/2003 | Pressly, Sr. et al. |
| 6,607,508 B2 | 8/2003 | Knauer |
| 6,623,459 B1 | 9/2003 | Doyle |
| 6,629,956 B1 | 10/2003 | Polidoro et al. |
| 6,629,957 B1 | 10/2003 | Wiklund |
| 6,629,959 B2 | 10/2003 | Kuracina et al. |
| 6,632,198 B2 | 10/2003 | Caizza |
| 6,635,032 B2 | 10/2003 | Ward, Jr. |
| 6,648,858 B2 | 11/2003 | Asbaghi |
| 6,673,044 B2 | 1/2004 | Righi et al. |
| 6,685,677 B2 | 2/2004 | Green |
| 6,689,106 B2 | 2/2004 | Bush, Jr. et al. |
| 6,692,470 B2 | 2/2004 | Sanpietro |
| 6,702,784 B1 | 3/2004 | Shedder et al. |
| 6,712,788 B2 | 3/2004 | Righi et al. |
| 6,716,191 B2 | 4/2004 | Sergio |
| 6,749,587 B2 | 6/2004 | Flaherty |
| 6,761,706 B2 | 7/2004 | Vaillancourt |
| 6,776,777 B2 | 8/2004 | Barrelle |
| 6,884,237 B2 | 4/2005 | Asbaghi |
| 6,918,889 B1 | 7/2005 | Brunel |
| 6,918,891 B2 | 7/2005 | Bressler et al. |
| 6,926,697 B2 | 8/2005 | Malenchek |
| 6,986,760 B2 | 1/2006 | Giambattista et al. |
| 6,997,901 B2 | 2/2006 | Popovsky |
| 7,001,364 B1 | 2/2006 | Farhi |
| 7,018,344 B2 | 3/2006 | Bressler et al. |
| 7,083,600 B2 | 8/2006 | Meloul |
| 7,101,351 B2 | 9/2006 | Crawford et al. |
| 7,118,552 B2 | 10/2006 | Shaw et al. |
| 7,144,388 B2 | 12/2006 | Crawford |
| 7,198,617 B2 | 4/2007 | Millerd |
| 7,201,740 B2 | 4/2007 | Crawford |
| 7,220,249 B2 | 5/2007 | Hwang et al. |
| 7,294,118 B2 | 11/2007 | Saulenas et al. |
| 7,300,416 B2 | 11/2007 | Botich et al. |
| 7,357,783 B2 | 4/2008 | Millerd |
| 7,422,573 B2 | 9/2008 | Wilkinson et al. |
| 7,462,169 B2 | 12/2008 | Follman et al. |
| 7,468,054 B2 | 12/2008 | Crawford et al. |
| 7,497,847 B2 | 3/2009 | Crawford et al. |
| 7,534,231 B2 | 5/2009 | Kuracina et al. |
| 7,540,858 B2 | 6/2009 | DiBiasi |
| 7,544,180 B2 | 6/2009 | Woehr |
| 7,553,293 B2 | 6/2009 | Jensen et al. |
| 7,578,805 B2 | 8/2009 | Hwang |
| 7,666,164 B2 | 2/2010 | Giambattista et al. |
| 7,666,168 B2 | 2/2010 | Millerd |
| 7,717,877 B2 | 5/2010 | Lavi et al. |
| 7,731,692 B2 | 6/2010 | Moos et al. |
| 7,811,259 B2 | 10/2010 | Klippenstein |
| 7,811,261 B2 | 10/2010 | Rubinstein et al. |
| 7,824,379 B2 | 11/2010 | Doyle |

(56) References Cited

U.S. PATENT DOCUMENTS

| | | | |
|---|---|---|---|
| 7,854,723 B2 | 12/2010 | Hwang et al. |
| 7,901,382 B2 | 3/2011 | Daily et al. |
| 7,985,216 B2 | 7/2011 | Daily et al. |
| 8,016,797 B2 | 9/2011 | Gratwohl et al. |
| 8,038,647 B2 | 10/2011 | Harding et al. |
| 8,038,654 B2 | 10/2011 | Lim et al. |
| 8,057,431 B2 | 11/2011 | Woehr et al. |
| 8,062,252 B2 | 11/2011 | Alheidt et al. |
| 8,066,678 B2 | 11/2011 | Vaillancourt et al. |
| 8,066,688 B2 | 11/2011 | Zinger et al. |
| 8,162,882 B2 | 4/2012 | Rubinstein et al. |
| 8,167,820 B2 | 5/2012 | Mahurkar |
| 8,172,810 B2 | 5/2012 | Liversidge |
| 8,246,588 B2 | 8/2012 | Gyrn |
| 8,298,180 B2 | 10/2012 | Meehan et al. |
| 8,328,766 B2 | 12/2012 | Liversidge |
| 8,357,104 B2 | 1/2013 | Moos et al. |
| 8,372,044 B2 | 2/2013 | Westbye et al. |
| 8,376,998 B2 | 2/2013 | Daily et al. |
| 8,425,460 B2 | 4/2013 | Cowe |
| 8,496,627 B2 | 7/2013 | Chelak et al. |
| 8,551,051 B2 | 10/2013 | Salto et al. |
| 8,556,855 B2 | 10/2013 | Zivkovic et al. |
| 8,617,119 B2 | 12/2013 | Liversidge |
| 8,632,500 B2 | 1/2014 | Knutsson et al. |
| 8,636,703 B2 | 1/2014 | Foshee et al. |
| 8,647,299 B2 | 2/2014 | Stamp |
| 8,657,803 B2 | 2/2014 | Helmerson et al. |
| 8,663,129 B2 | 3/2014 | Allen et al. |
| 8,663,174 B2 | 3/2014 | Laiken et al. |
| 8,672,895 B2 | 3/2014 | Kuracina et al. |
| 8,672,901 B2 | 3/2014 | Bollenbach et al. |
| 8,708,969 B2 | 4/2014 | Carlyon |
| 8,721,599 B2 | 5/2014 | Livkovic et al. |
| 8,728,035 B2 | 5/2014 | Warring et al. |
| 8,747,361 B2 | 6/2014 | Millerd et al. |
| 8,814,833 B2 | 8/2014 | Farrell et al. |
| 8,821,453 B2 | 9/2014 | Doyle et al. |
| 8,827,961 B2 | 9/2014 | Emmott et al. |
| 8,834,422 B2 | 9/2014 | Walker et al. |
| 8,845,594 B2 | 9/2014 | Jennings |
| 8,888,742 B2 | 11/2014 | Harms et al. |
| 8,939,942 B2 | 1/2015 | Perot et al. |
| 8,945,065 B2 | 2/2015 | Torris et al. |
| 8,945,067 B2 | 2/2015 | McLoughlin et al. |
| 8,961,470 B2 | 2/2015 | Schraga |
| 8,968,240 B2 | 3/2015 | Erskine |
| 8,968,241 B2 | 3/2015 | Liversidge |
| 8,979,792 B2 | 3/2015 | Lev et al. |
| 8,979,794 B2 | 3/2015 | Chevallier |
| 9,022,022 B2 | 5/2015 | Edwards et al. |
| 9,022,990 B2 | 5/2015 | Chevallier et al. |
| 9,044,552 B2 | 6/2015 | Schraga |
| 2002/0004650 A1 | 1/2002 | Kuracina et al. |
| 2003/0028171 A1 | 2/2003 | DeHarde et al. |
| 2003/0036725 A1 | 2/2003 | Lavi et al. |
| 2003/0050608 A1 | 3/2003 | Brown |
| 2003/0078546 A1 | 4/2003 | Jensen |
| 2003/0144630 A1 | 7/2003 | Chang et al. |
| 2003/0144631 A1 | 7/2003 | Doyle et al. |
| 2003/0149403 A1 | 8/2003 | Barker et al. |
| 2003/0181868 A1 | 9/2003 | Swenson |
| 2003/0212380 A1* | 11/2003 | Barrelle ............ A61M 5/326 604/506 |
| 2004/0039340 A1 | 2/2004 | Prais et al. |
| 2004/0116853 A1* | 6/2004 | Halseth ............ A61M 5/283 604/110 |
| 2004/0116874 A1 | 6/2004 | Lourenco et al. |
| 2004/0127857 A1 | 7/2004 | Shemesh et al. |
| 2004/0193110 A1 | 9/2004 | Giambattista et al. |
| 2004/0215150 A1 | 10/2004 | Shue et al. |
| 2004/0236281 A1 | 11/2004 | Popovsky |
| 2005/0096595 A1* | 5/2005 | Restelli ............ A61M 5/326 604/198 |
| 2005/0096597 A1 | 5/2005 | Crawford et al. |
| 2005/0119627 A1 | 6/2005 | Crawford |
| 2005/0148943 A1* | 7/2005 | Chevalier ............ A61M 5/326 604/198 |
| 2005/0187522 A1 | 8/2005 | Miller |
| 2005/0267410 A1 | 12/2005 | Koska |
| 2006/0089594 A1 | 4/2006 | Landau |
| 2006/0095010 A1 | 5/2006 | Westbye |
| 2006/0189935 A1 | 8/2006 | Janek et al. |
| 2006/0211985 A1 | 9/2006 | Wang |
| 2006/0229562 A1 | 10/2006 | Marsh et al. |
| 2007/0060893 A1 | 3/2007 | Mahurkar |
| 2007/0073224 A1 | 3/2007 | Dries |
| 2007/0129675 A1 | 6/2007 | Summerville et al. |
| 2007/0293819 A1 | 12/2007 | Giambattista et al. |
| 2008/0021389 A1 | 1/2008 | Runfola |
| 2008/0183140 A1 | 7/2008 | Paproski et al. |
| 2008/0249477 A1 | 10/2008 | Paproski et al. |
| 2009/0005742 A1 | 1/2009 | Liversidge |
| 2009/0227956 A1 | 9/2009 | Emmott et al. |
| 2009/0299295 A1 | 12/2009 | Rubinstein et al. |
| 2009/0326477 A1 | 12/2009 | Liversidge |
| 2010/0042053 A1 | 2/2010 | Dillard, III |
| 2010/0179487 A1 | 7/2010 | Woehr |
| 2010/0298770 A1 | 11/2010 | Rubinstein et al. |
| 2011/0196339 A1 | 8/2011 | Hirschel et al. |
| 2011/0208126 A1 | 8/2011 | Riemelmoser |
| 2012/0316466 A1 | 12/2012 | Crawford et al. |
| 2012/0316467 A1 | 12/2012 | Kolb |
| 2013/0018312 A1 | 1/2013 | Neale |
| 2013/0204200 A1 | 8/2013 | Roberts et al. |
| 2013/0331796 A1 | 12/2013 | Wozencroft |
| 2015/0094659 A1 | 4/2015 | Schraga |

FOREIGN PATENT DOCUMENTS

| | | |
|---|---|---|
| EP | 1159979 A2 | 12/2001 |
| EP | 1205173 A3 | 5/2002 |
| EP | 1273316 A1 | 1/2003 |
| EP | 0916354 B1 | 3/2003 |
| EP | 1344544 A1 | 9/2003 |
| EP | 1346739 A1 | 9/2003 |
| EP | 1362609 A1 | 11/2003 |
| EP | 1535640 A1 | 6/2005 |
| EP | 1201261 B1 | 2/2006 |
| EP | 1480707 B1 | 7/2006 |
| EP | 1558310 B1 | 6/2008 |
| EP | 1970086 A2 | 9/2008 |
| EP | 2119464 A1 | 11/2009 |
| EP | 2139544 A1 | 1/2010 |
| EP | 2037989 B1 | 9/2010 |
| EP | 2438952 A1 | 4/2012 |
| EP | 2462969 A1 | 6/2012 |
| EP | 2533835 | 12/2012 |
| EP | 2552522 | 2/2013 |
| EP | 2572741 A1 | 3/2013 |
| EP | 2572742 A1 | 3/2013 |
| EP | 2572745 A1 | 3/2013 |
| EP | 2578189 A1 | 4/2013 |
| EP | 2578255 A1 | 4/2013 |
| EP | 2586479 A1 | 5/2013 |
| EP | 2646089 | 10/2013 |
| EP | 2735333 A1 | 5/2014 |
| EP | 1379301 B1 | 6/2014 |
| EP | 2598030 B1 | 3/2015 |
| EP | 2085104 B1 | 4/2015 |
| GB | 2463071 A | 3/2010 |
| WO | 9512425 A2 | 5/1995 |
| WO | 9531234 A1 | 11/1995 |
| WO | 9857689 A1 | 12/1998 |
| WO | 9906100 A2 | 2/1999 |
| WO | 0018465 A1 | 4/2000 |
| WO | 0018466 A1 | 4/2000 |
| WO | 0176665 A1 | 10/2001 |
| WO | 02072171 A2 | 9/2002 |
| WO | 03041766 A2 | 5/2003 |
| WO | 03082385 A1 | 10/2003 |
| WO | 2004060445 A2 | 7/2004 |
| WO | 2004069302 A2 | 8/2004 |
| WO | 2005079891 A1 | 9/2005 |

(56) References Cited

FOREIGN PATENT DOCUMENTS

| | | |
|---|---|---|
| WO | 2005113039 A1 | 12/2005 |
| WO | 2006060710 A2 | 6/2006 |
| WO | 2006072135 A1 | 7/2006 |
| WO | 2006082350 A1 | 8/2006 |
| WO | 2006111806 A2 | 10/2006 |
| WO | 2007047200 A1 | 4/2007 |
| WO | 2008047372 A2 | 4/2008 |
| WO | 2008084063 A1 | 7/2008 |
| WO | 2008097217 A1 | 8/2008 |
| WO | 2008116688 A1 | 10/2008 |
| WO | 2008127195 A1 | 10/2008 |
| WO | 2008131091 A2 | 10/2008 |
| WO | 2009039022 A2 | 3/2009 |
| WO | 2009067646 A1 | 5/2009 |
| WO | 2010059502 A2 | 5/2010 |
| WO | 2010061405 A2 | 6/2010 |
| WO | 2010076569 A2 | 7/2010 |
| WO | 2010104779 A1 | 9/2010 |
| WO | 2010110743 A1 | 9/2010 |
| WO | 2010126432 A1 | 11/2010 |
| WO | 2011018408 A1 | 2/2011 |
| WO | 2011022621 A1 | 2/2011 |
| WO | 2011043714 A1 | 4/2011 |
| WO | 2011101382 A2 | 8/2011 |
| WO | 2011101383 A1 | 8/2011 |
| WO | 2011117283 A1 | 9/2011 |
| WO | 2011123659 A1 | 10/2011 |
| WO | 2011146166 A1 | 11/2011 |
| WO | 2012000832 A1 | 1/2012 |
| WO | 2012000833 A1 | 1/2012 |
| WO | 2012000834 A1 | 1/2012 |
| WO | 2012000835 A1 | 1/2012 |
| WO | 2012000836 A1 | 1/2012 |
| WO | 2012049468 A2 | 4/2012 |
| WO | 2012093069 A1 | 7/2012 |
| WO | 2012093071 A1 | 7/2012 |
| WO | 2012093072 A1 | 7/2012 |
| WO | 2012093073 A1 | 7/2012 |
| WO | 2013037744 A1 | 3/2013 |

\* cited by examiner

CONTACT TRIGGER RELEASE NEEDLE GUARD

CROSS REFERENCE TO RELATED APPLICATIONS

This application is a divisional application of U.S. application Ser. No. 13/671,309, filed on Nov. 7, 2012 and now issued as U.S. Pat. No. 9,579,468, which claims the benefit of U.S. Provisional Application No. 61/556,674, filed Nov. 7, 2011.

FIELD

The embodiments provided herein relate generally to safety systems for syringes, and more particularly to a needle guard for a syringe that includes an automatically activated shield for covering a needle of the syringe.

BACKGROUND INFORMATION

Medication is often dispensed using a medicine cartridge, such as a glass syringe, having a barrel with a needle at one end and a plunger slidably inserted into the other end and coupled to a rubber stopper. Such cartridges are often referred to as "pre-filled syringes" because they may contain a specific dosage or volume medication when they are initially provided, as compared to conventional syringes that are furnished empty and filled by the user before making an injection.

The glass syringe and rubber stopper have, for years, provided an ideal drug storage closure having unique properties of impermeability to oxygen, low extractables, biocompatibility, durability, etc. However, they are both formed by processes that do not lend themselves to tight geometrical tolerances. Tight tolerances were not originally needed by these devices because they were not used mechanically with other devices.

Due to the risk of communicable diseases, a number of syringes and adapters have been developed that are intended to prevent accidental needle sticks and/or inadvertent reuse of a syringe. Conventional passive anti-needle stick safety devices for prefilled syringes must mount to the syringe but not interfere excessively with the force required to move the plunger rod during injection nor prevent the full travel of the plunger rod. The safety mechanism necessarily must be triggered toward the end of administration of the drug (near the end of the plunger rod travel). However, since virtually all safety devices locate the syringe against the safety device at a point under the syringe finger flange, the operability of the safety device tends to be dependent on the tolerances of the syringe and stopper.

In addition, because conventional passive anti-needle stick safety devices for prefilled syringes tend to mount to or on the barrel of the syringe, the safety devices tend to obscure the contents of the syringe and must be applied post filling of the syringe.

Prefilled syringes tend to be shipped to pharma customers as ready-to-fill syringes, which are ones that have been thoroughly cleaned inside and outside after the forming processes and attachment of a needle and then placed in sealed tubs that are then sterilized and shipped to the pharma customers ready for filling with a medicine. The syringe tubs may contain 100 to 160 syringes each with a geometrical spacing and access that is consistent with established syringe handling equipment. A safety device applied to the syringe must not obscure the optical inspection systems that are in place to check the syringes prior to filling them with medication.

Accordingly, it would be desirable to have a needle guard for a syringe having the safety device triggering mechanism independent of the syringe and stopper tolerances, and that assembles to the syringe without adversely affecting the syringe position with respect to the syringe handling tub or the way the handling equipment conveys the syringes during filling and packaging nor impedes the inspection processes.

SUMMARY

The systems and methods described herein are directed to a needle guard for a syringe having the safety device triggering mechanism independent of the syringe and stopper tolerances. A contact trigger release needle guard device described herein is an anti-needle stick device designed to be attached to the distal end of a ready-to-fill syringe. The needle guard device includes a lock collar and a device shield moveable relative to the lock collar. The device shield is biased relative to the lock collar by a spring. The lock collar interfaces with a syringe neck and bulbus to attach the needle guard device to the ready-to-fill syringe. With the removal of a needle shield subassembly comprising rigid and soft needle shields, the lock collar and device shield are free to move proximally along the syringe neck and interact with the syringe step down area triggering the device shield to move relative to the lock collar from a first position, where a syringe sharp such as a needle is exposed, to a second position where the needle is shielded or covered.

In use, a device user removes the needle shield subassembly, inserts the syringe sharp, such as a needle, into an injection site and pushes down on the syringe past the point of initial contact of the device shield with the skin, and up to the point where the lock collar and device shield have moved proximally along the syringe neck until the lock collar is prevented from moving further proximally by the syringe step down. As the needle guard device moves proximally along the syringe neck, retention arms of the device shield interface with the syringe step down to deflect outwards to disengage from the lock collar triggering the device shield to move under a bias to the second or needle shielded position.

In an alternative embodiment, both tactile and audible feedback signalling device activation is incorporated into the needle guard device. A feedback system includes feedback arms, which are pushed passed feedback tabs during device activation preferably as the retention arms are disengaged from the lock collar.

In another alternative embodiment, the lock collar may be vertically fixed to the syringe and include a lock collar ring with lock collar tabs that can freely slide relative to the lock collar.

Other systems, methods, features and advantages of the invention will be or will become apparent to one with skill in the art upon examination of the following figures and detailed description.

BRIEF DESCRIPTION OF THE FIGURES

The details of the invention, including fabrication, structure and operation, may be gleaned in part by study of the accompanying figures, in which like reference numerals refer to like parts. The components in the figures are not necessarily to scale, emphasis instead being placed upon illustrating the principles of the invention. Moreover, all

DETAILED DESCRIPTION

Figure 1:
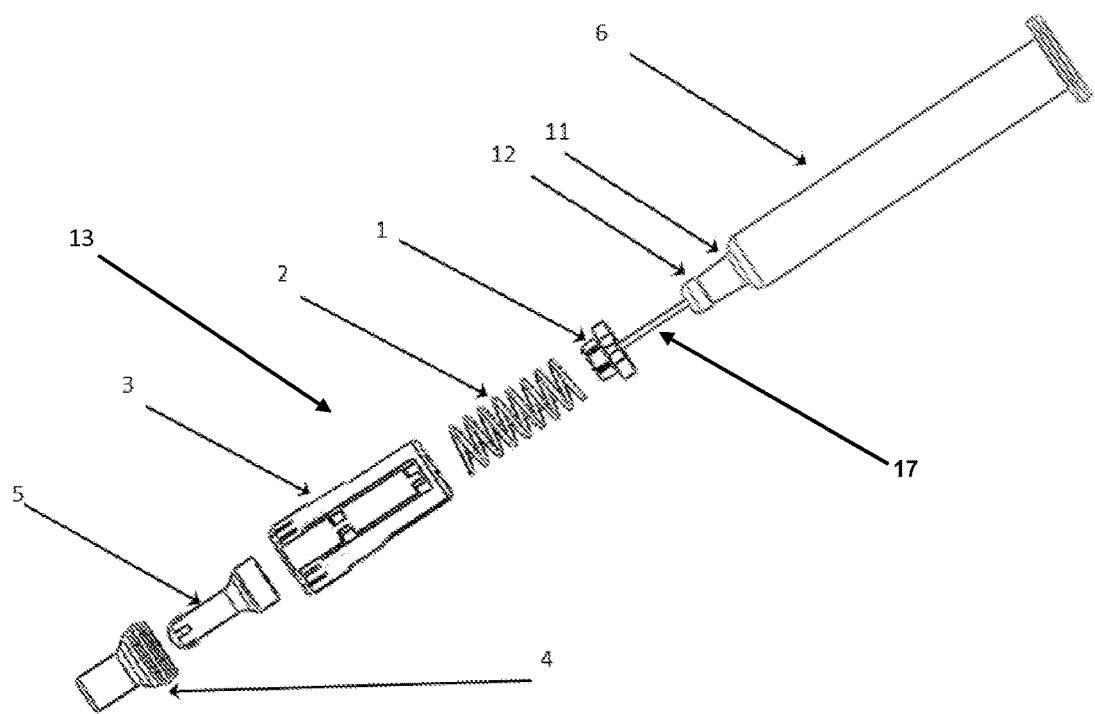
FIG. 1 is an exploded isometric view of a needle guard device with a ready-to-fill syringe.

The systems and methods described herein are directed to a needle guard for a syringe having the safety device triggering mechanism independent of the syringe geometry. Turning now to the figures, FIGS. 1-23 show an embodiment of a contact trigger release needle guard. The needle guard described herein is an anti-needle stick safety device designed to be attached to the distal end of a prefilled syringe in its ready-to-fill state. As depicted in FIG. 1, the needle guard device 13 which couples to a syringe 6 (depicted in its ready-to-fill state), is comprised of five (5) parts which include: a lock collar 1, a compression spring 2, a device shield 3, a rigid needle shield 4, and a soft needle shield 4.

Figure 2:
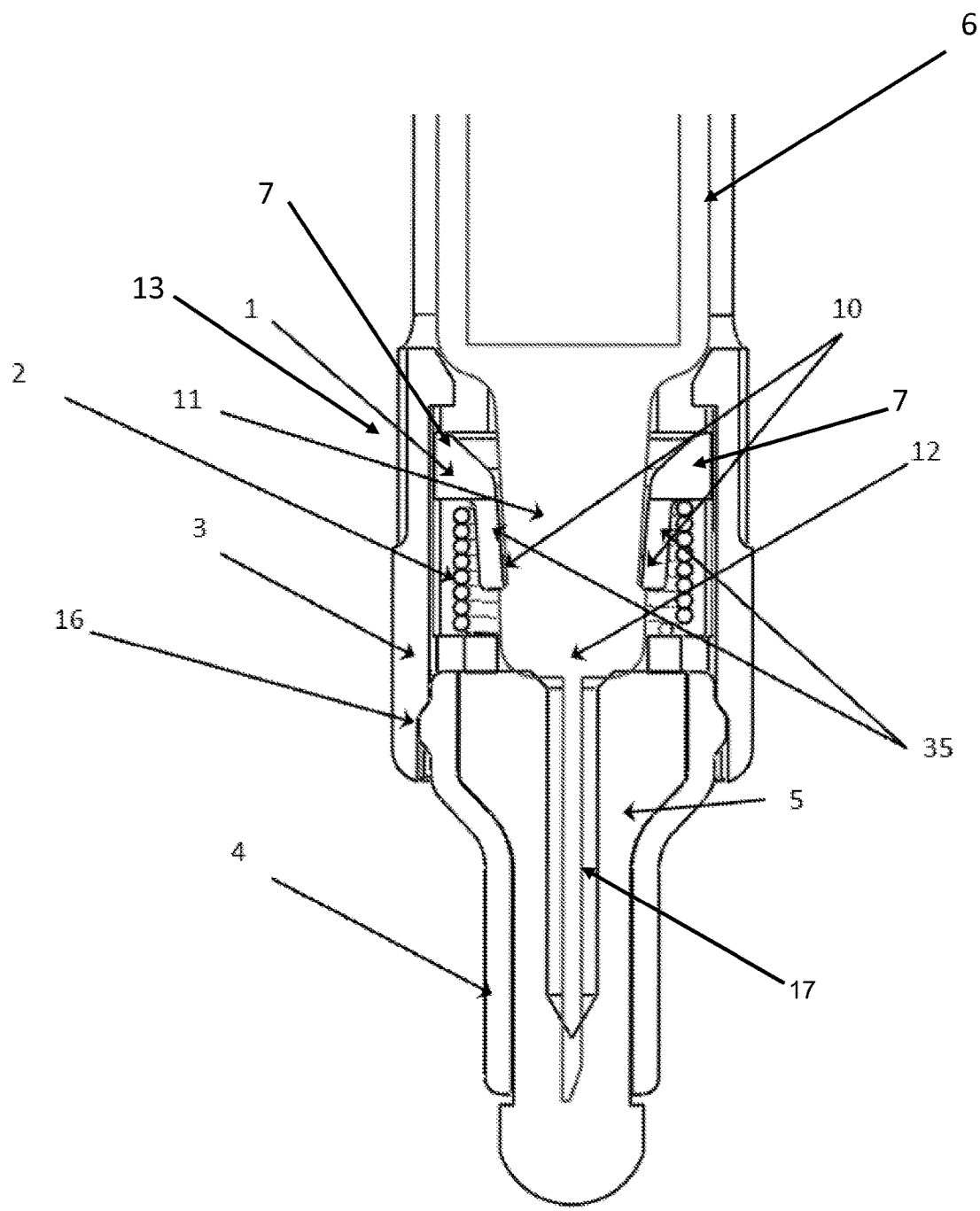
FIG. 2 is a partial section view of the needle guard device with the syringe in the fully assembled pre-loaded state prior to use.
Figure 3:
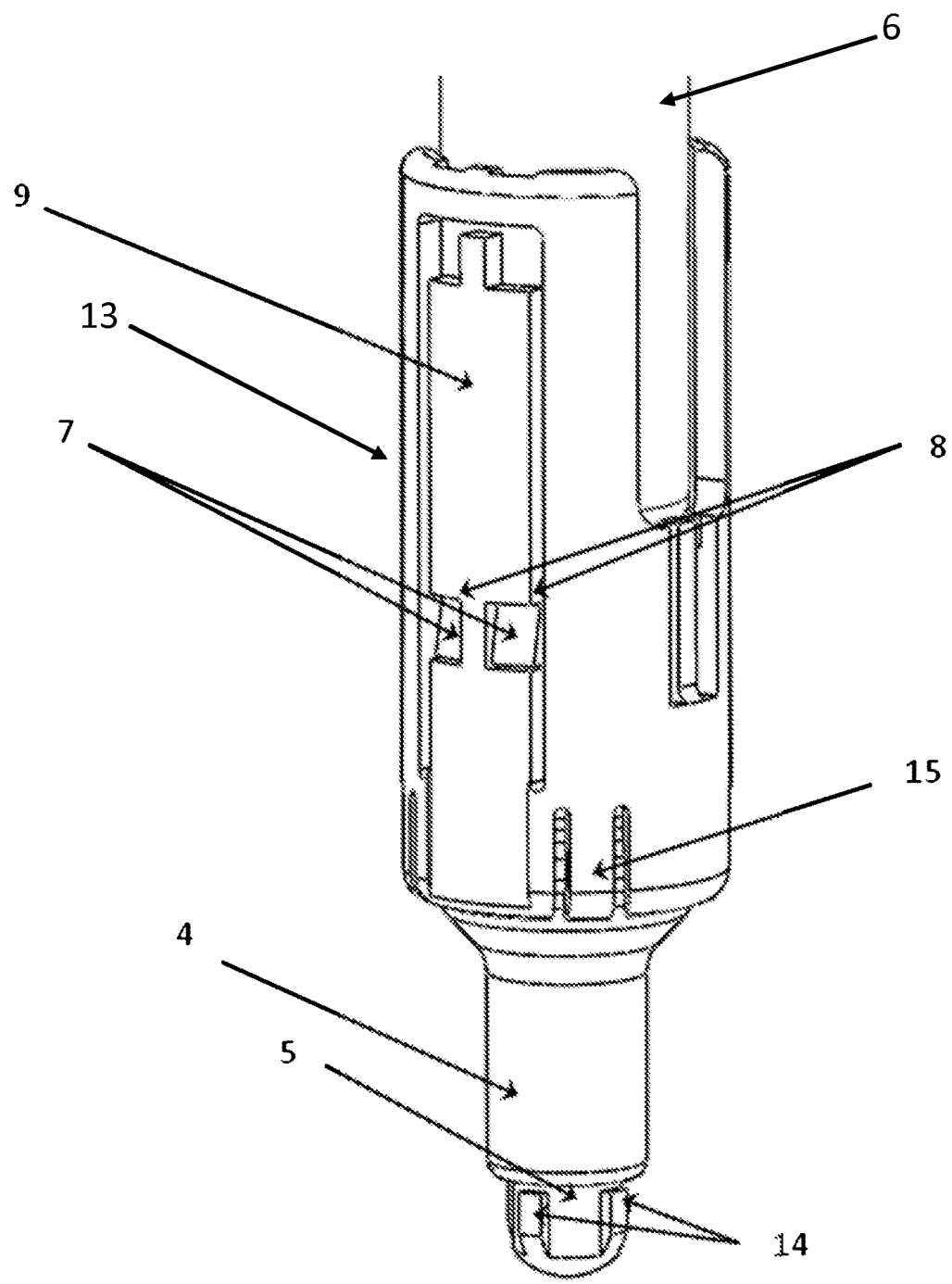
FIG. 3 is a partial isometric view of the needle guard device attached to the syringe in the fully assembled pre-loaded state prior to use.
Figure 4:
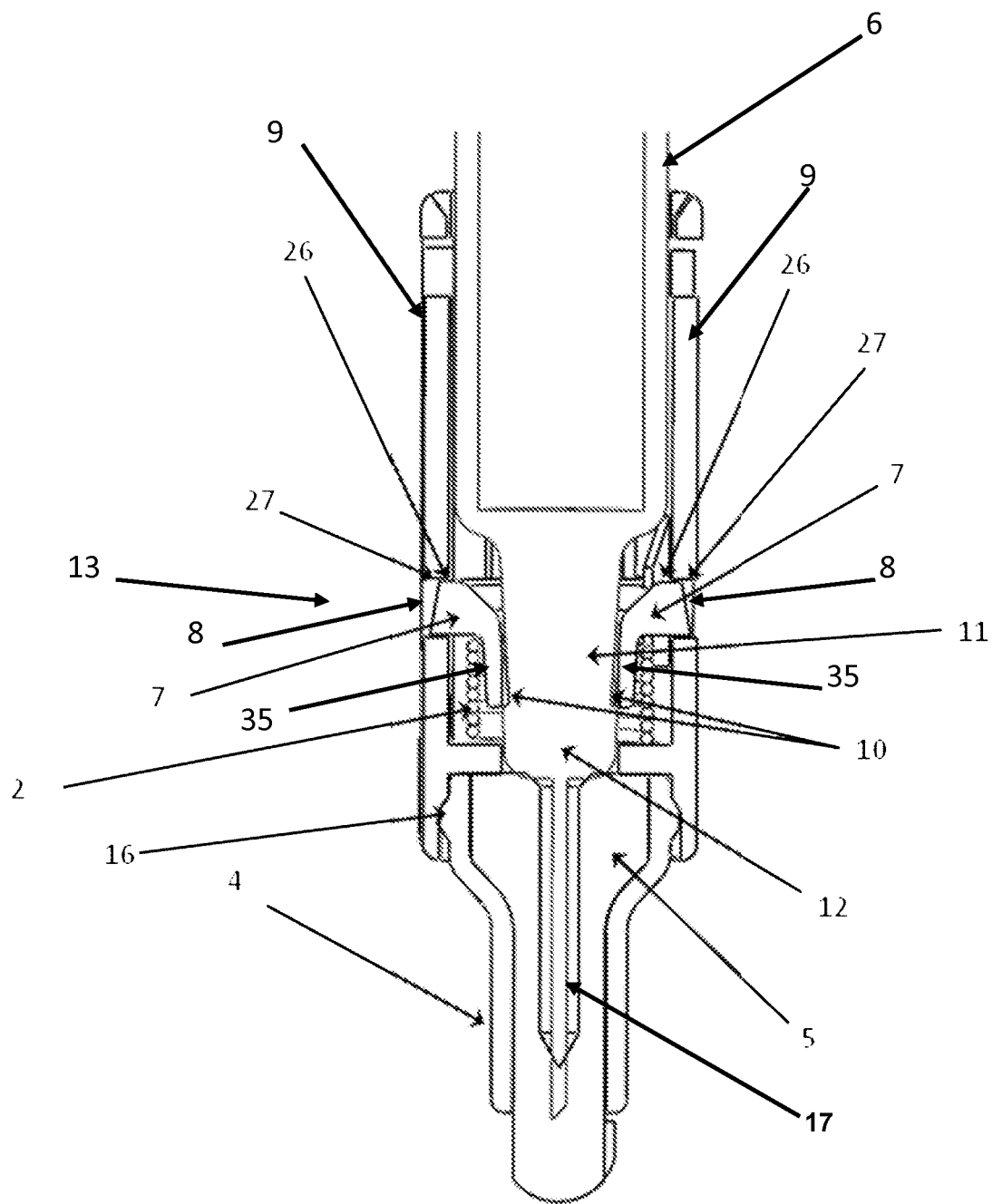
FIG. 4 is a partial section view of the needle guard device with the syringe neck through the lock collar stop tabs in the fully assembled pre-loaded state prior to use.
Figure 5:
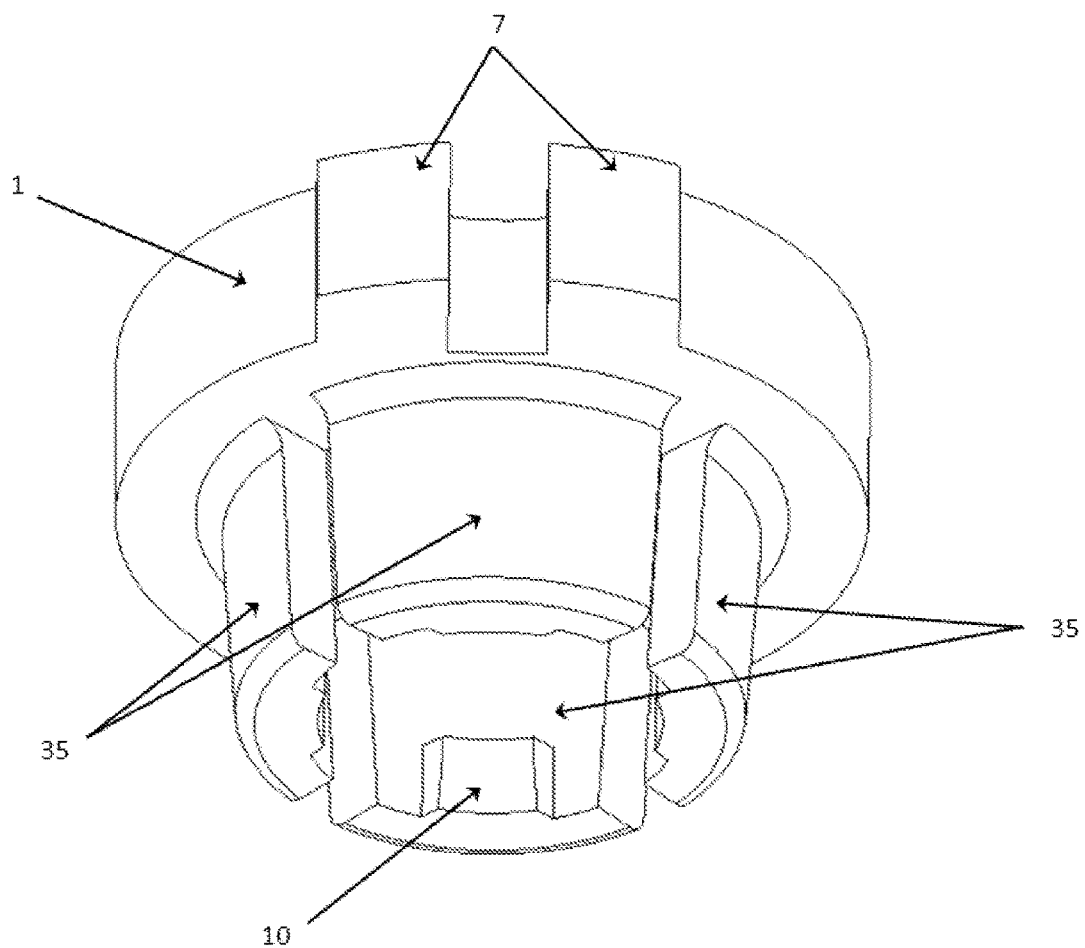
FIG. 5 is an isometric view of the lock collar showing the lock collar retaining arms for retention to the syringe bulbus.
Figure 6:
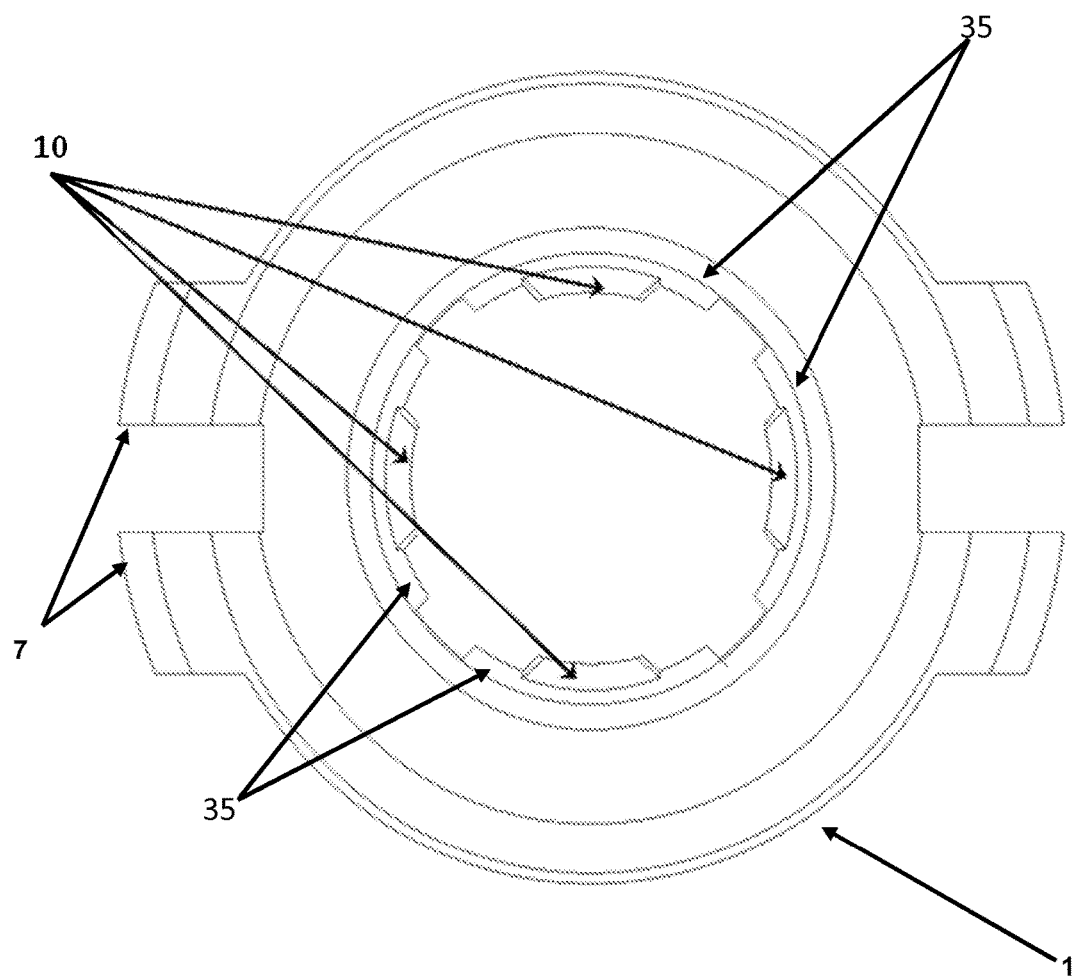
FIG. 6 is a bottom view of the lock collar.
Figure 7:
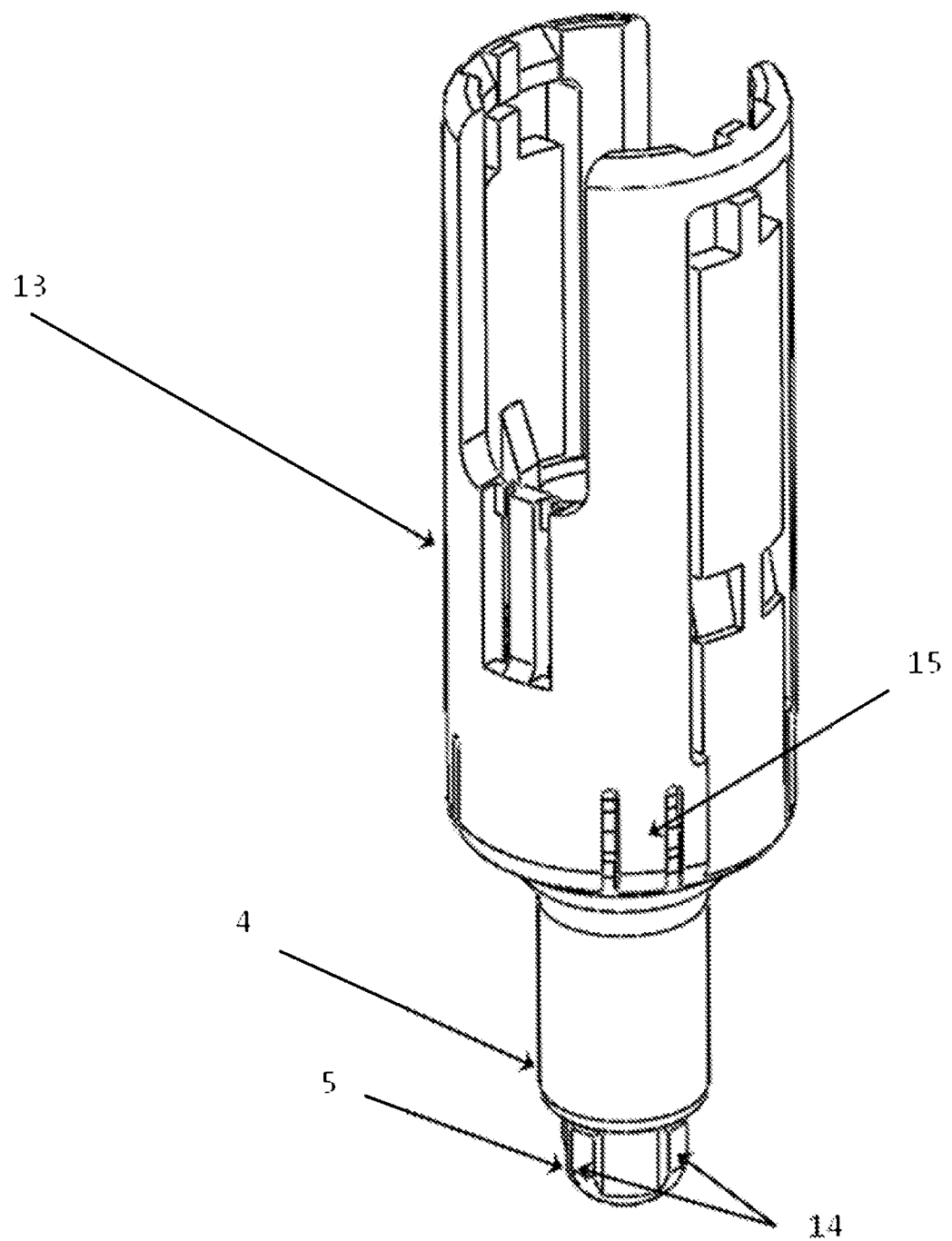
FIG. 7 is an isometric view of the needle guard device without the syringe in the fully assembled pre-loaded state prior to use.
Figure 8:
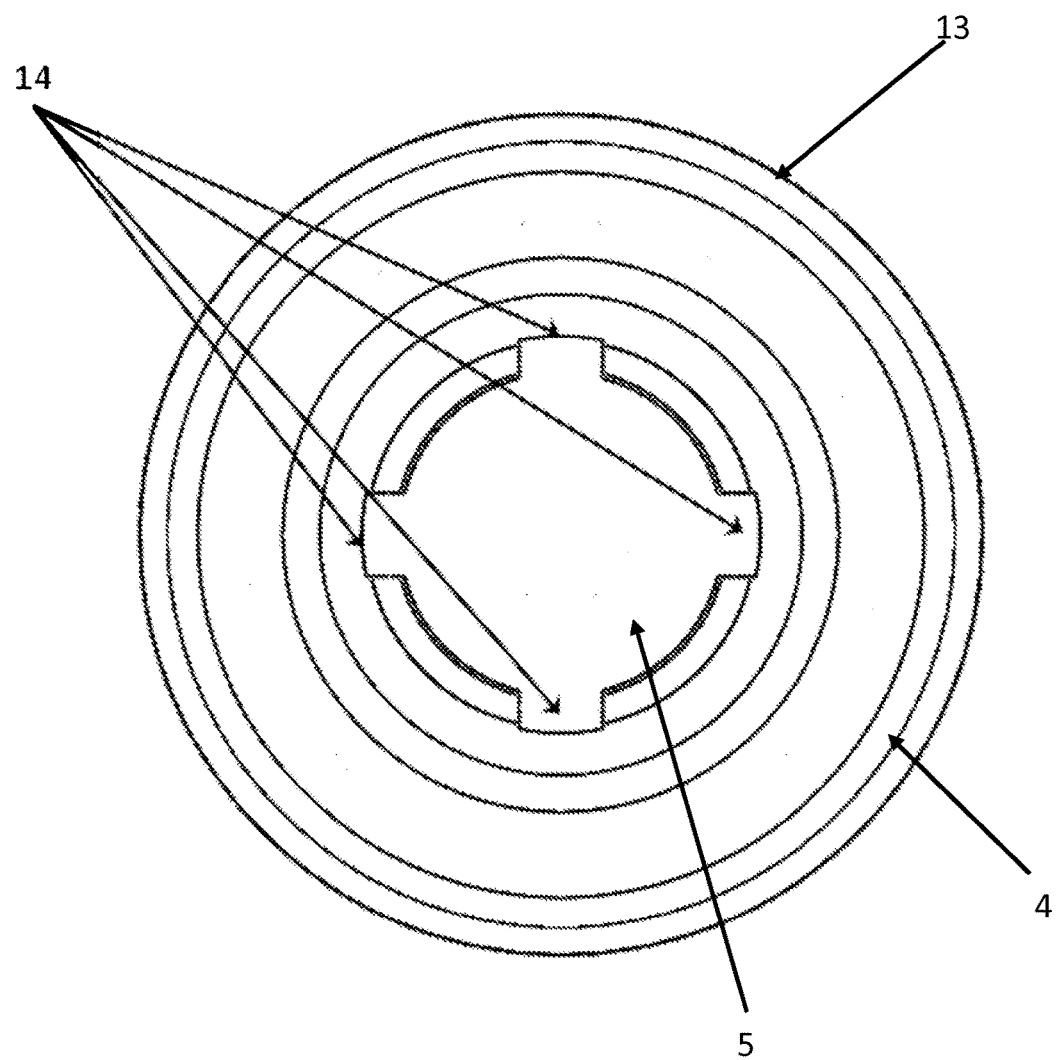
FIG. 8 is a bottom view of the needle guard device showing the compressible tabs of the soft needle shield.
Figure 9:
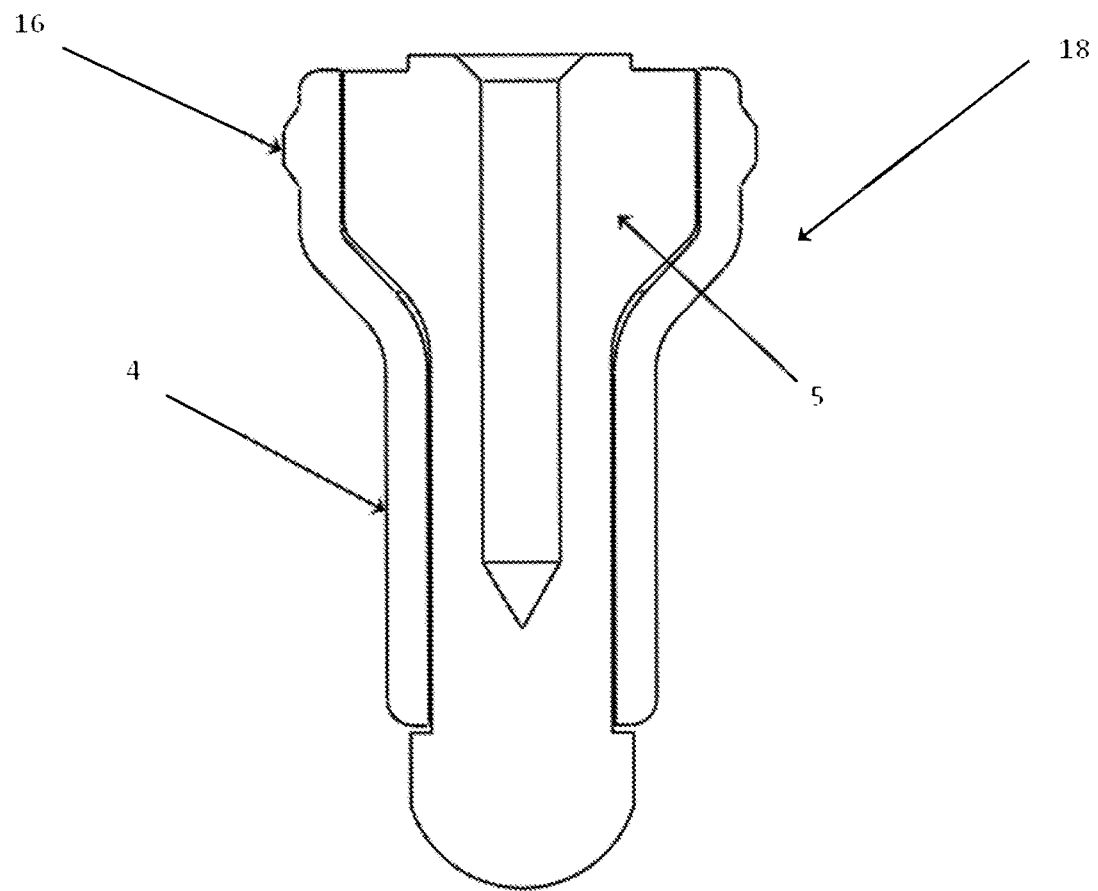
FIG. 9 is a partial section view of a needle shield subassembly comprised of a soft needle shield and a rigid needle shield.

As depicted in FIGS. 2-4, the needle guard device 13 is delivered to the end user in a pre-loaded state, with the spring 2 compressed between the device shield 3 and lock collar 1. The lock collar 1 has two lock tabs 7 on each side, which, as shown in FIG. 3, fit within two openings or cutouts 8 in each of the retention arms 9 of the device shield 3. As depicted in FIG. 4, the seat area 27 of the retention arms 9 rest on the horizontal surface 26 of the lock collar tabs 7, in the pre-loaded state, which lock the lock collar 1 and device shield 3 assembly together in a first position with a syringe sharp 17 extending beyond the distal end of the device shield. The force of the compression spring 2 holds the assembly in tension. As depicted in FIGS. 5 and 6, the lock collar 1 contains four pads 10 internally located at the ends of lock collar retaining arms 35, which, as shown in FIGS. 2 and 4, interface with the syringe neck 11 and bulbus 12 to attach the needle guard device 13 to the syringe 6. The inner diameter of the lock collar 1 is defined by the lock collar pads 10 and are of a similar diameter to the base of the syringe neck 11 but less than the diameter of the bulbus 12. Consequently, during assembly of the needle guard device 13 onto the syringe 6, the lock collar pads 10 force the lock collar retaining arms 35 to flex over the bulbus 12 and relax around the syringe neck 11 for retention of the device 13 on the syringe 6 as shown in FIGS. 2 and 4.

Figure 10:
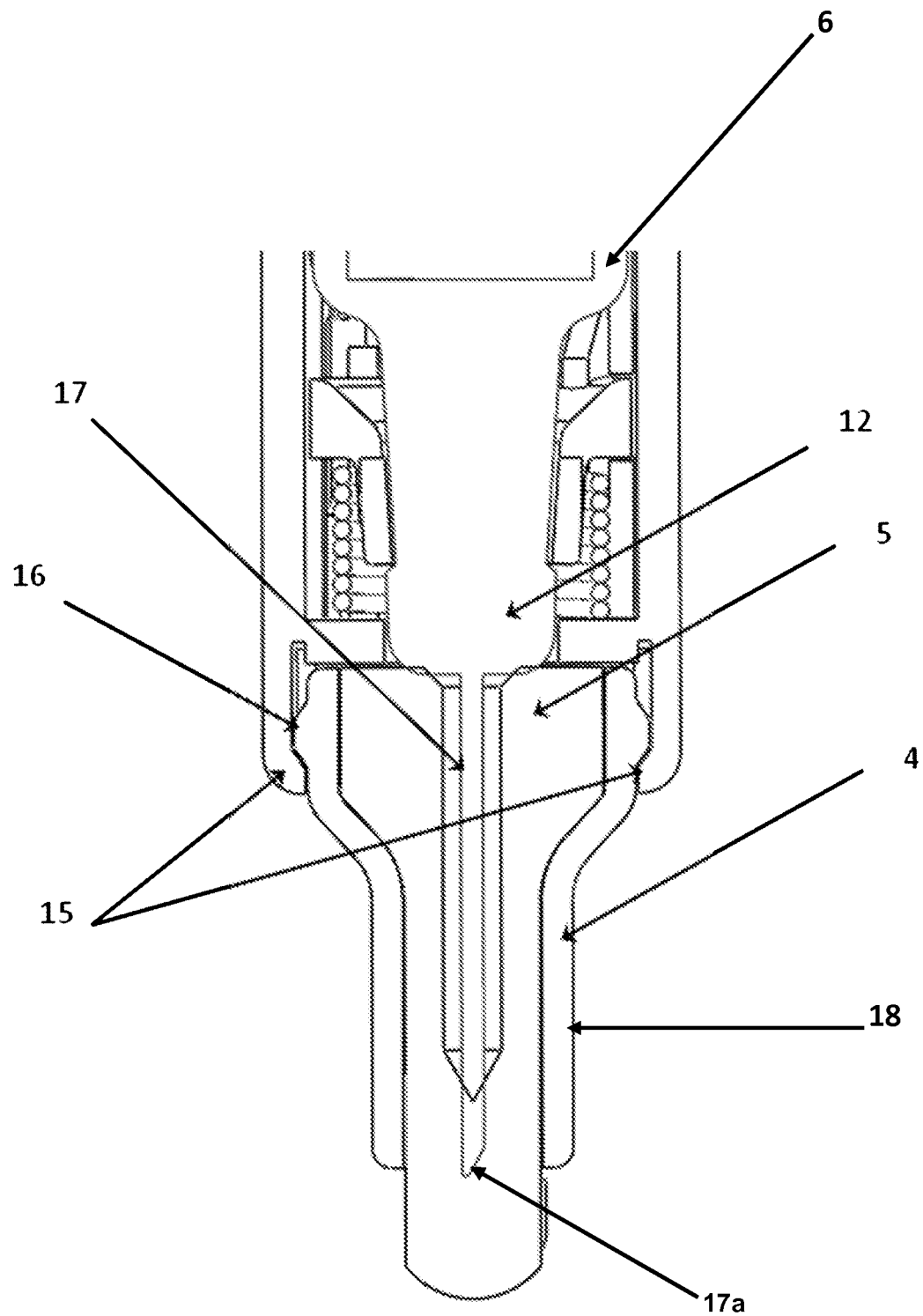
FIG. 10 is a partial section view through the passive retaining arms of the device shield showing the connection of the rigid needle shield to the device shield and the sealing surface of the soft needle shield against the bulbus of the syringe.

The rigid needle shield 4, comprised of a thermoplastic, and the soft needle shield 5, comprised of an elastomer, as shown in FIGS. 3, 7, 8, and 9 are locked with each other vertically via compressible tabs 14 located at the distal end of the soft needle shield 5. The soft needle shield 5 may be inserted into the rigid needle shield 4 by forcefully pushing the distal end of the soft needle shield 5 through the smaller diameter opening in the rigid needle shield 4. The rigid needle shield 4 and soft needle shield 5 subassembly 18 is releasably attached to the device shield 3 via flexible retaining arms 15 and an annular ring 16 on the proximal end of the rigid needle shield 4 as shown in FIG. 10. When assembled to the device shield 3, the soft needle shield 5 interferes with and compresses against the bulbus 12 of the syringe 6 creating a seal, which keeps the sharp (needle) 17 of the syringe 6 as well as the contents of the syringe 6 sterile prior to removal of the needle shield subassembly 18. At the distal end of the soft needle shield 5. The syringe sharp 17 protrudes into the elastomer material protecting the tip 17a of syringe sharp 17.

Figure 11:
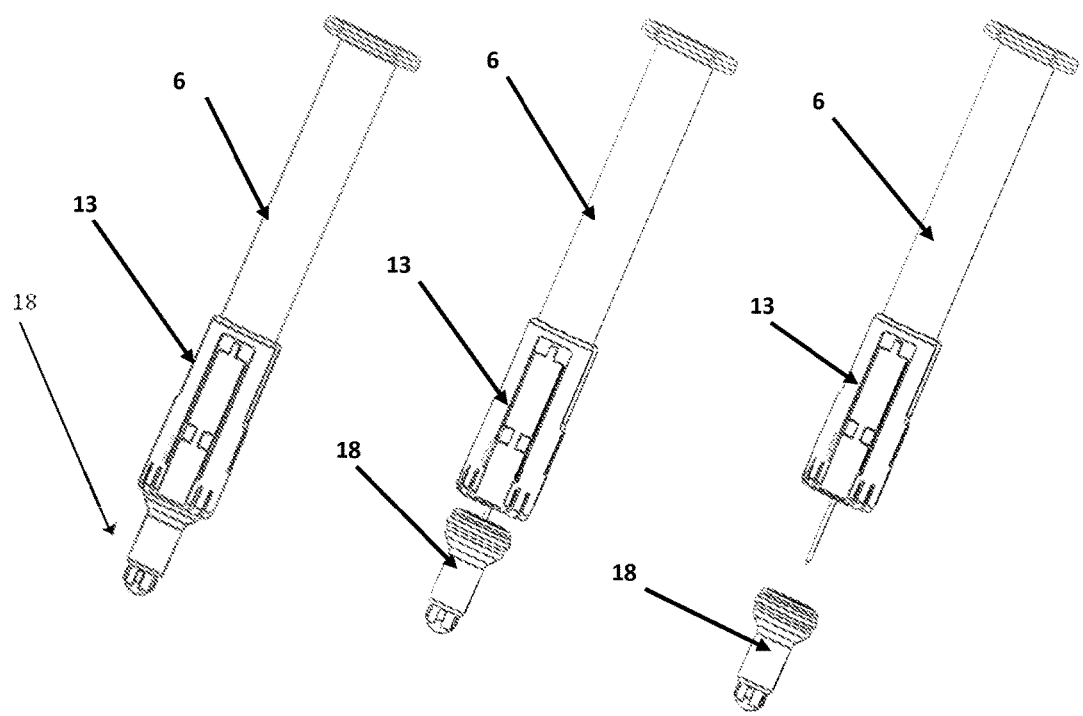
FIG. 11 is an isometric view of the needle guard device showing the sequential progression of the removal of the needle shield subassembly.
Figure 12:
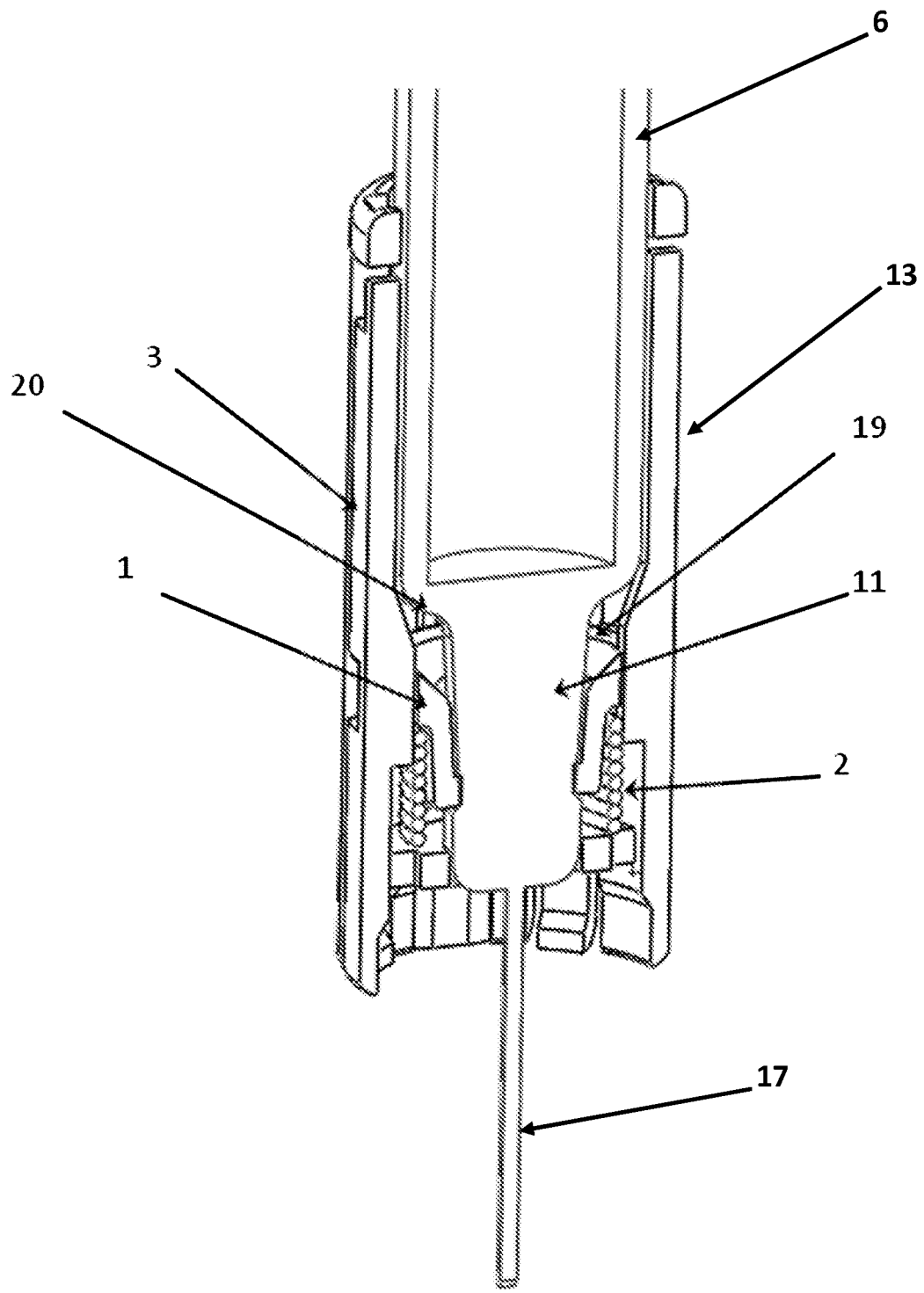
FIG. 12 is an isometric partial section view of the needle guard device with the needle shield subassembly removed and illustrates the ability of the needle guard device to move proximally along the syringe neck during needle insertion via a gap between the lock collar and syringe step down area.

Prior to performing an injection, a device user forcefully pulls out the needle shield subassembly 18, as shown in FIG. 11, pulling the annular ring 16 past the retaining arms 15. With the needle shield subassembly 18 removed from the needle guard device 13, as shown in FIG. 12, the lock collar 1, device shield 3, and spring 2 are free to move proximally along the syringe neck 11. As depicted in FIG. 12, there is a small gap 19 between the lock collar 1 and a stepped down area 20 of the syringe 6, which allows for such proximal movement. When the needle shield subassembly 18 is in place, as depicted in FIG. 10, such proximal movement along the syringe neck 11 is deterred due to the connection between the rigid needle shield 4 and the device shield 3, as well as the compression contact between the syringe bulbus 12 and the soft needle shield 5.

Figure 13:
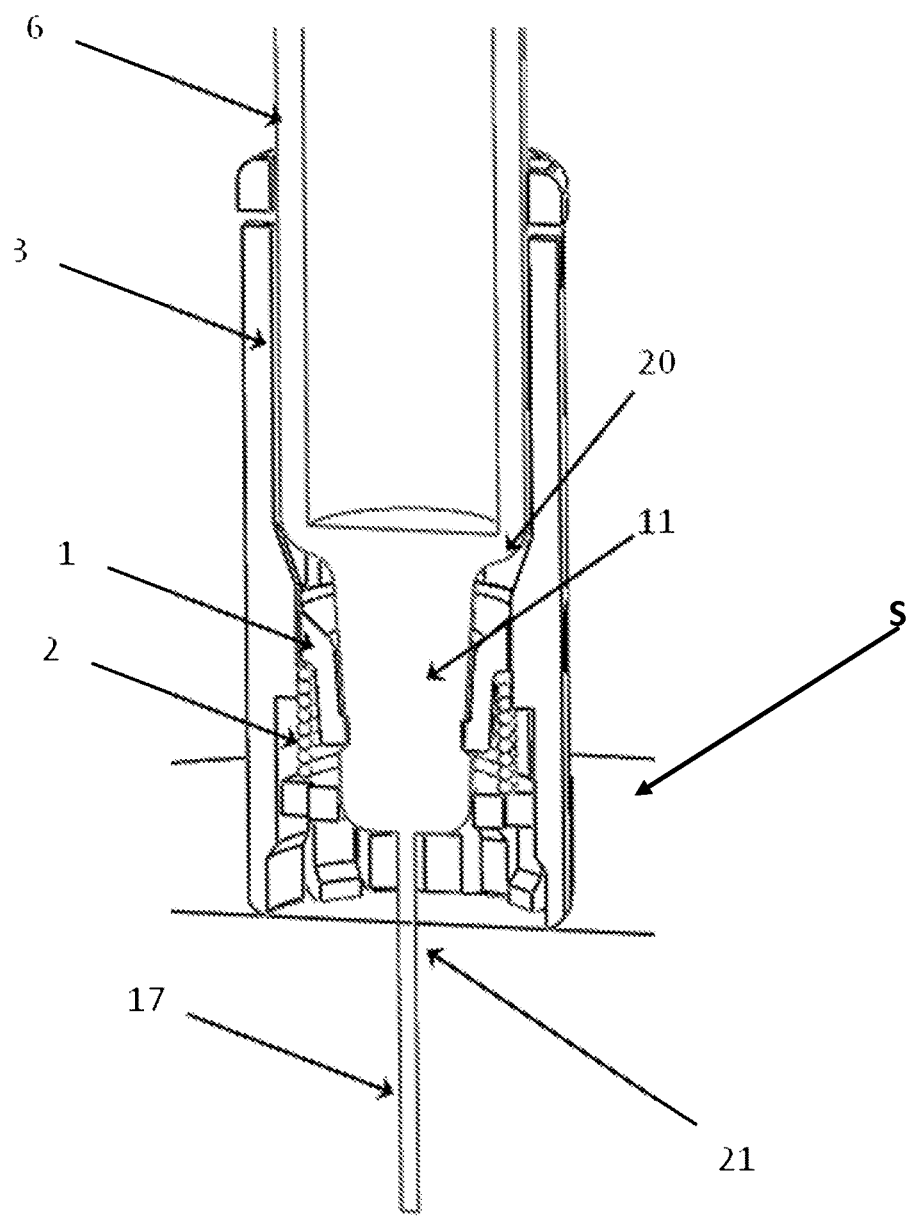
FIG. 13 is an isometric partial section view of the needle guard device with the syringe sharp inserted into an injection site with the device shield initially touching the injection site.
Figure 14:
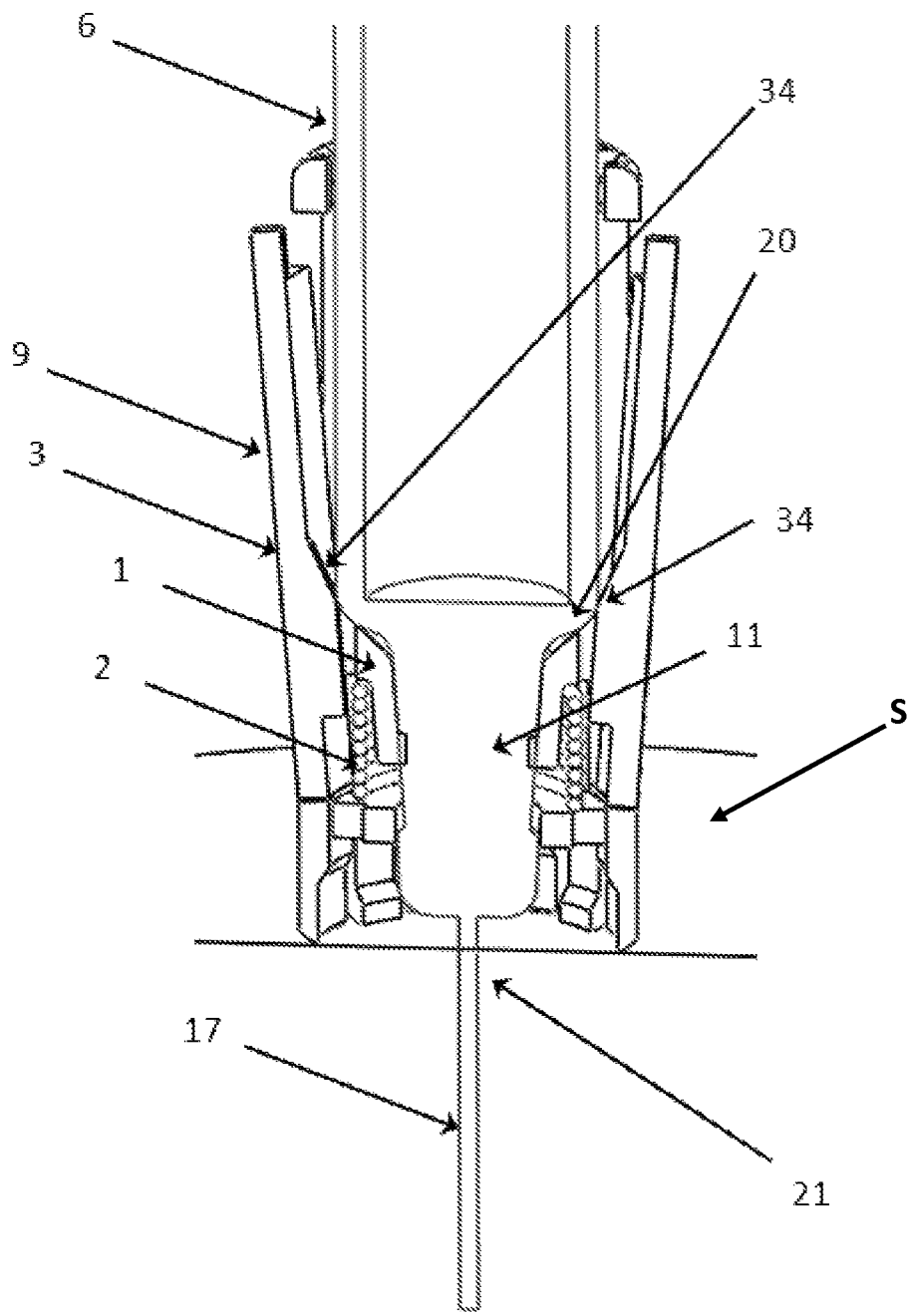
FIG. 14 is an isometric partial section view of the needle guard device with the syringe sharp completely inserted into the injection site with flex arms bent outward as a result of their interaction with the syringe step down area and the lock collar is positioned all the way up the syringe neck in contact with the syringe step down.
Figure 15:
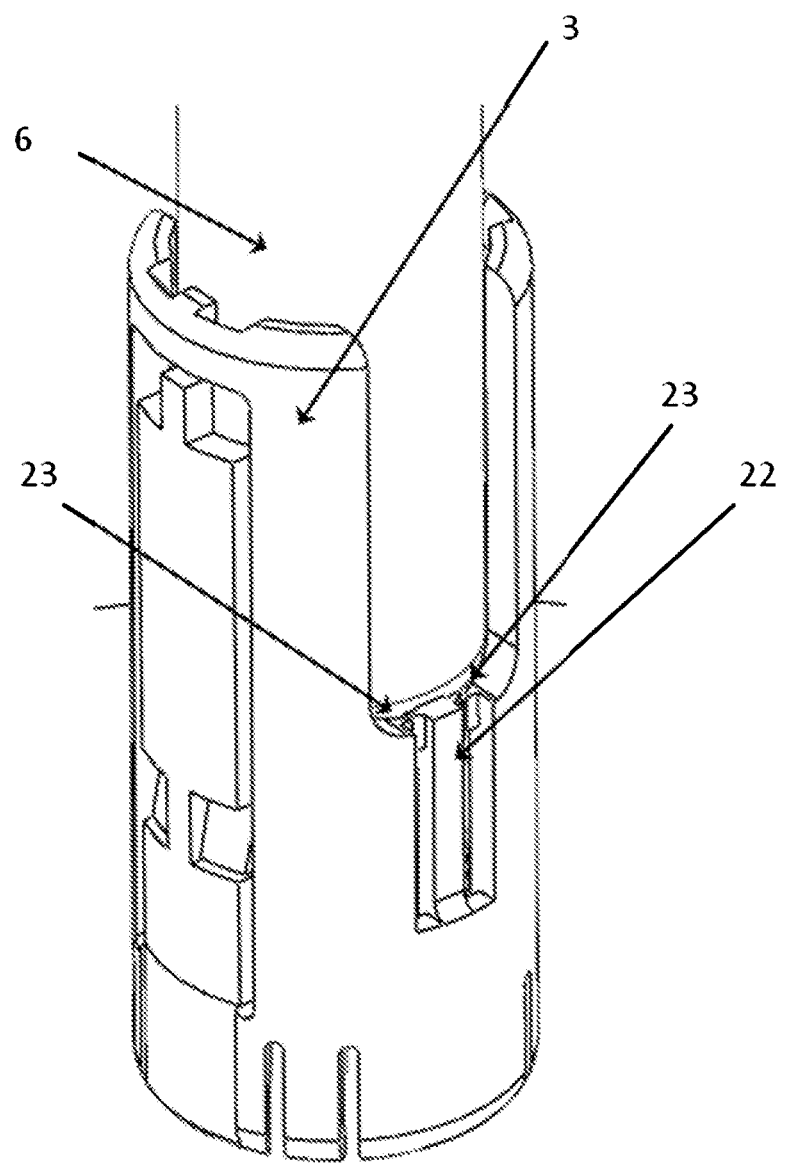
FIG. 15 is an isometric partial view of the needle guard device and the syringe with the needle shield subassembly removed and showing an audible and tactile feedback arm integrated with the needle guard device.
Figure 16:
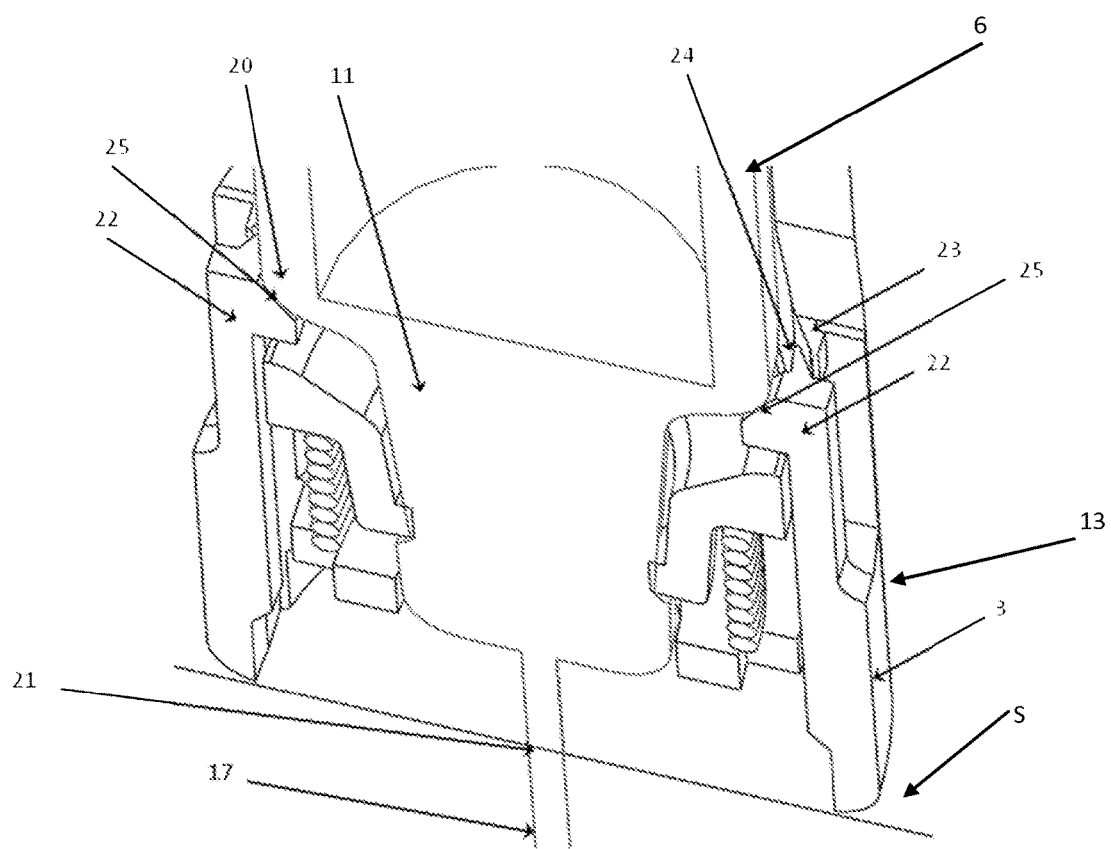
FIG. 16 is an isometric partial section view through the feedback arms of the needle guard device with the syringe sharp inserted into the injection site and the device shield initially touching the injection site, prior to safety activation of the needle guard device.
Figure 17:
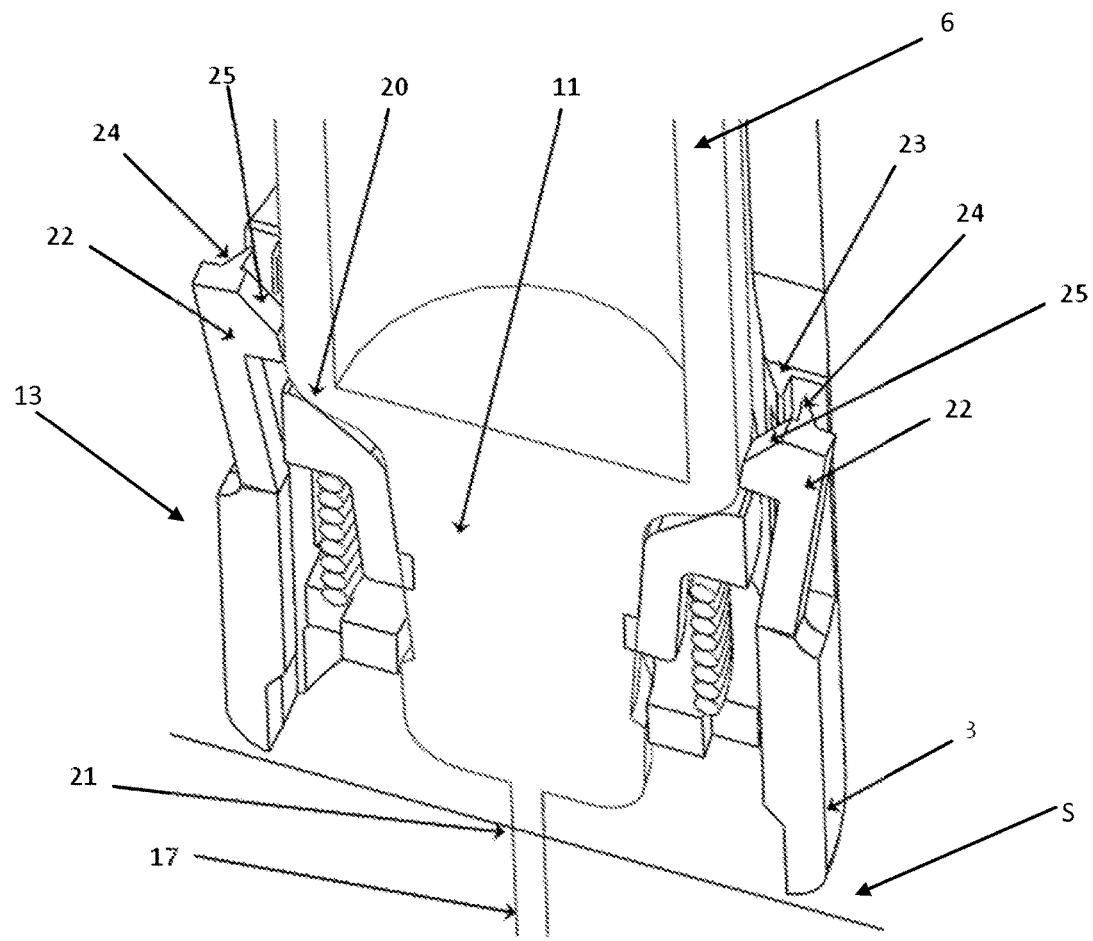
FIG. 17 is an isometric partial section view through the feedback arms of the needle guard device with the syringe sharp completely inserted into the injection site and the needle guard device activated. The feedback arms are shown bent outward due to their interaction with the syringe step down area during needle insertion, with the feedback arm ears pushed past the device shield angled tabs.
Figure 18:
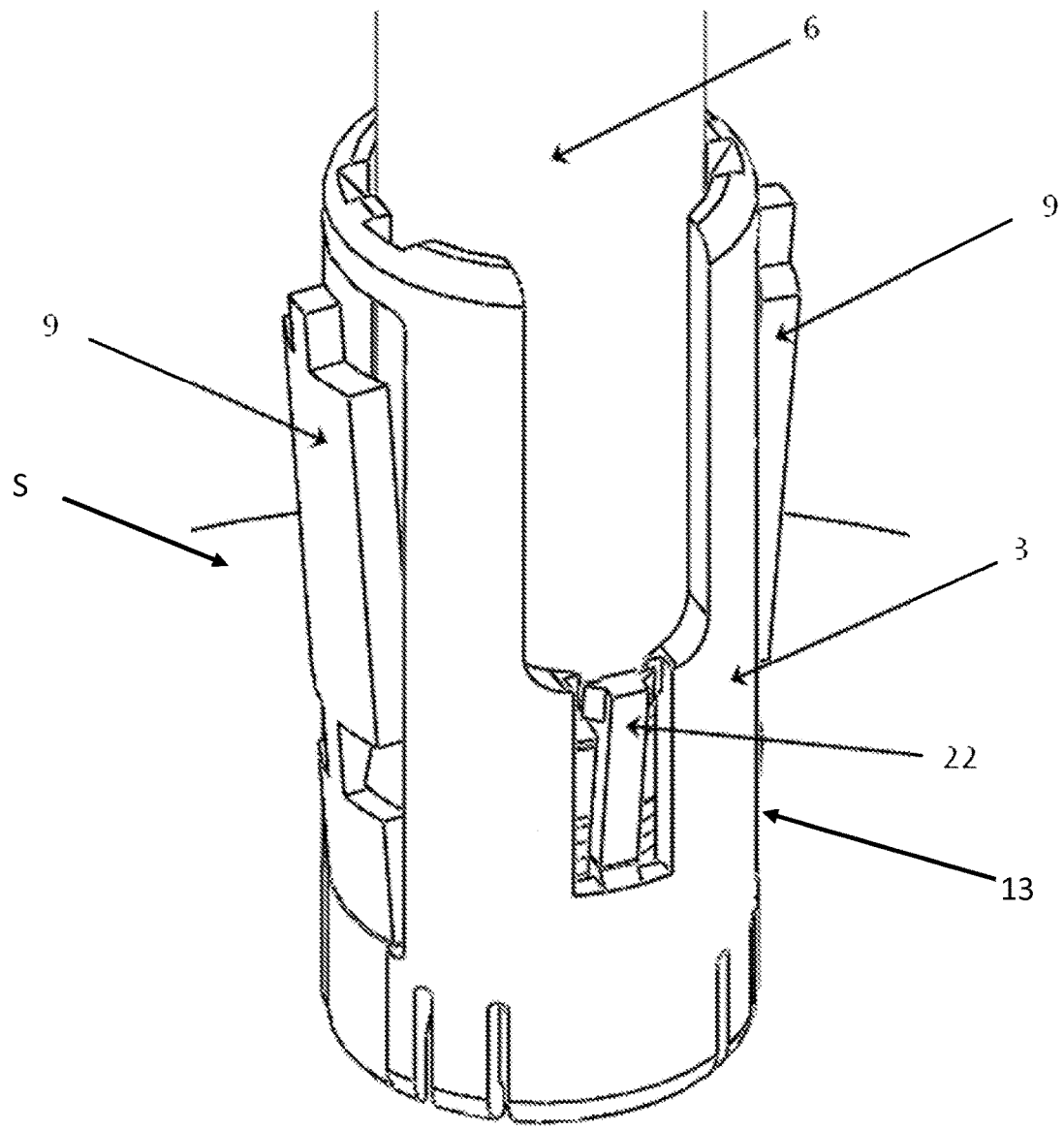
FIG. 18 is an isometric partial view of the needle guard device after the safety device has been activated with the flex arms and flexible feedback arms bent outward and syringe fully inserted into the injection site.
Figure 19:
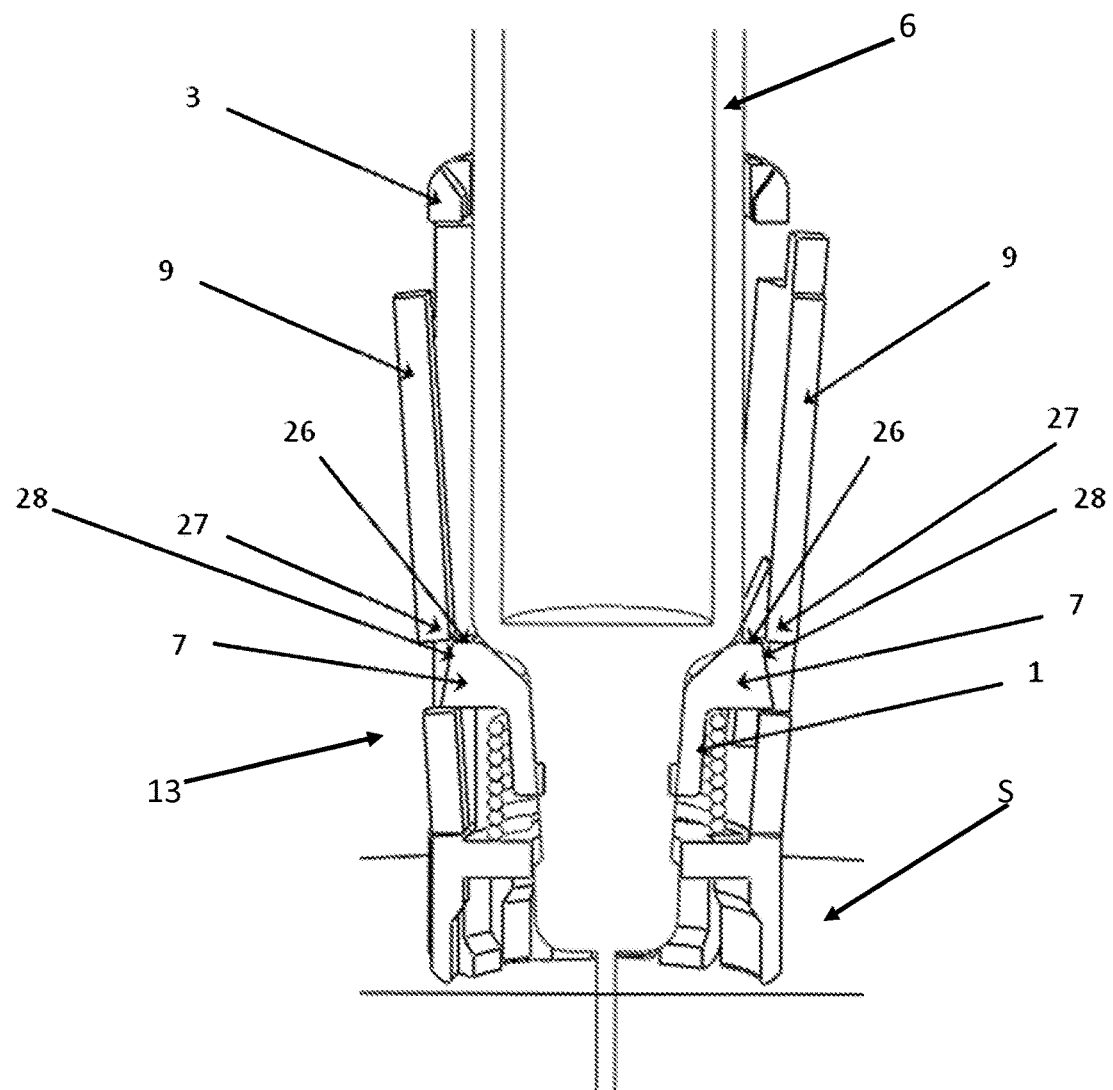
FIG. 19 is a partial section view of the needle guard device through the lock collar tabs showing the retention arms bent outward after full syringe sharp insertion with the retention arms in contact with the angled surface of the lock collar tabs enabling the device shield to freely move relative to the collar distally along the syringe to shield the syringe sharp as it is extracted from the injection site.

When performing an injection as shown in FIGS. 13 through 21, a device user first inserts the syringe sharp 17 into an injection site 21. The user pushes down on the syringe 6 past the point of initial contact of the device shield 3 with the skin S as shown in FIG. 13, and up to the point where the lock collar 1, spring 2 and device shield 3 have moved proximally along the syringe neck 11 until the lock collar 1 abuts the syringe step down 20 as shown in FIG. 14. Referring to FIGS. 14, 18 and 19, as the needle guard device 13 travels proximally along the syringe neck 11, chamfered rib 34 (FIG. 14) of the retention arms 9 of the device shield 3 interact with the syringe step down 20, causing the retention arms 9 to flex or deflect radially outwards. The user will know at this point that the safety device is activated because the retention arms 9 of the device shield 3 are bent radially outward from the needle guard device 13.

Additionally, as depicted in FIGS. 15-18, it is also possible to incorporate both tactile and audible feedback of device activation into the needle guard device 13 by means of feedback arms 22, which are caused to flex and push through angled tabs 23 present within the device shield 3 during device activation as the syringe sharp 17 is inserted into the injection site 21. As the syringe sharp 17 is inserted into the injection site 21 and the device shield 3 travels proximally along the syringe neck 11, the feedback arms 22, as shown in FIG. 16, interact with the syringe step down area 20 via a chamfered surface 25, deflecting the feedback arms 22 radially outward. As the feedback arms 22 push outward as shown in FIGS. 16-18, the feedback arm ears 24 contact and push past the device shield angled tabs 23 creating audible and tactile feedback that the needle guard device 13 has been activated.

Figure 20:
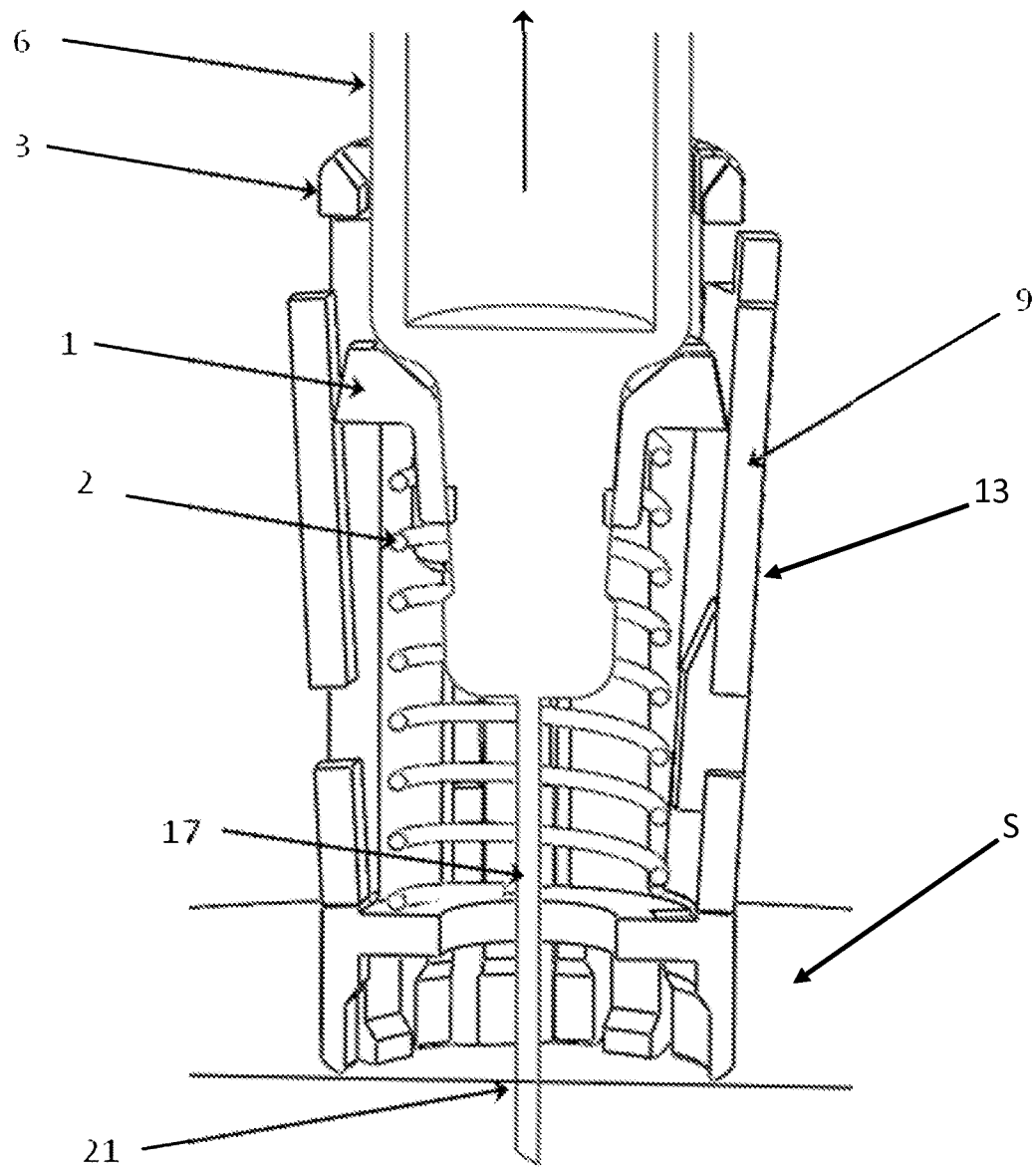
FIG. 20 is an isometric partial section view of the needle guard device through the lock collar tabs as the syringe is extracted from the injection site and the syringe sharp is almost completely removed as the spring acts on the device shield to keep it against the injection site as the syringe is removed and the retention arms move distally along the lock collar tabs.
Figure 21:
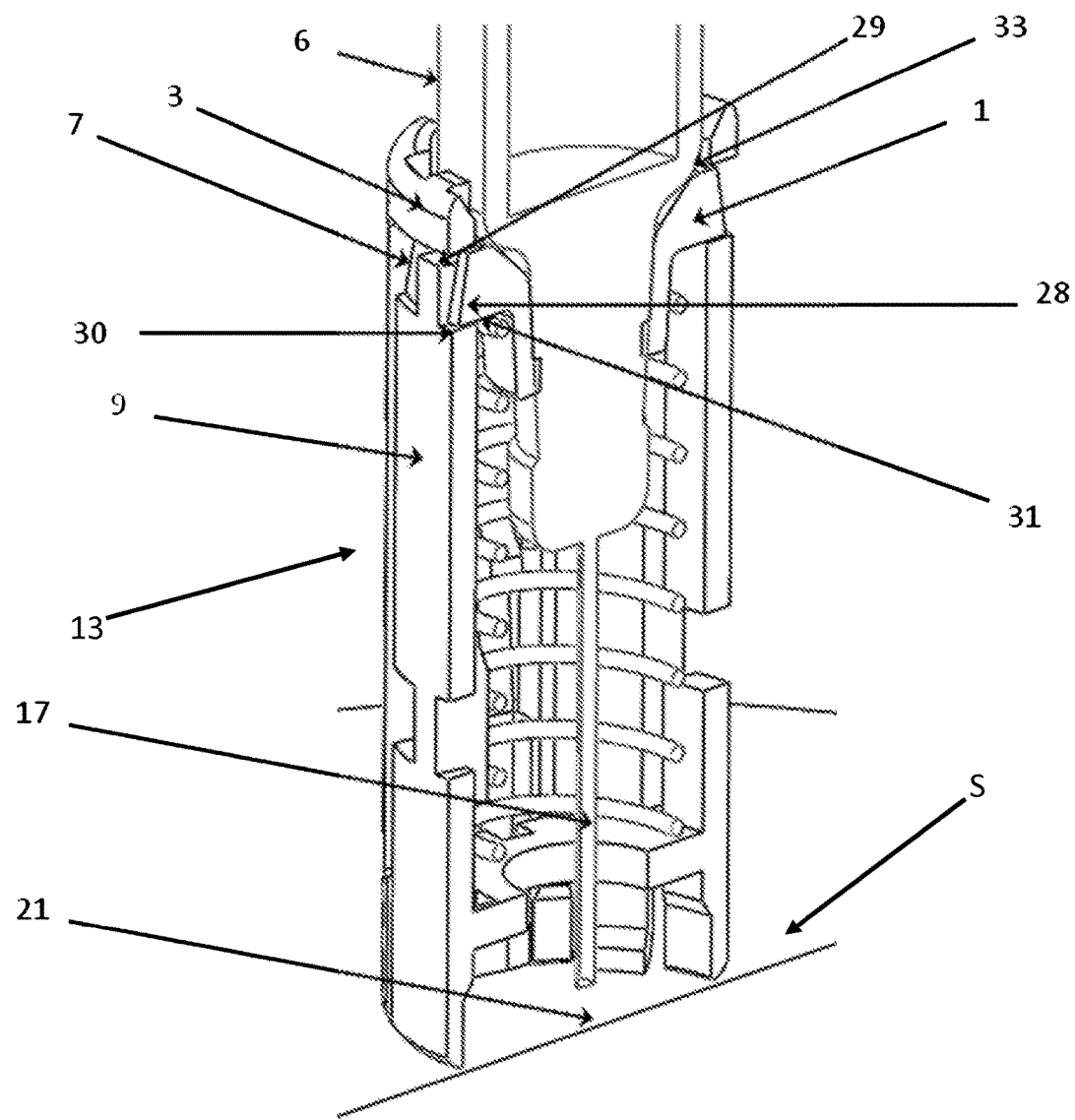
FIG. 21 is an isometric partial section view of the needle guard device through the lock collar tabs after the syringe sharp has been fully retracted from the injection site and the retention arms have resiled into place under the lock collar tabs to prevent the device shield from moving proximally and locking the device shield in the second position in a needle stick safe state.
Figure 22:
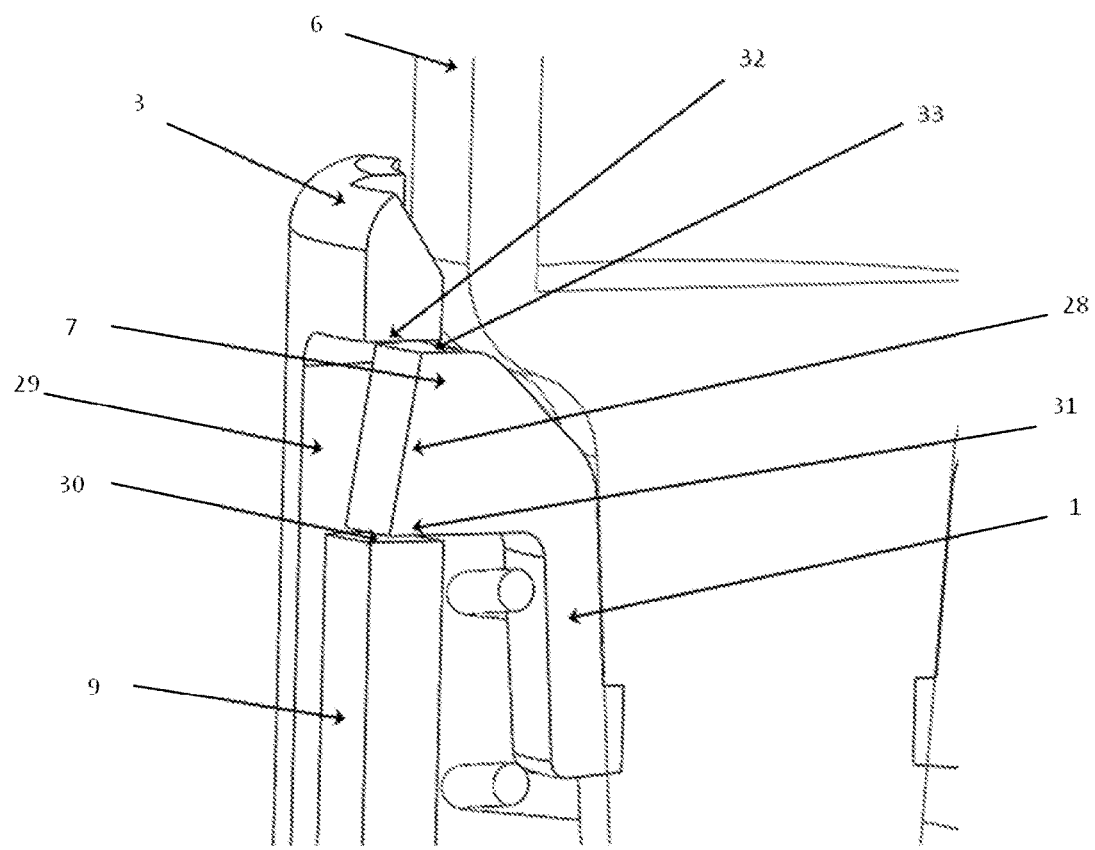
FIG. 22 is an enlarged isometric partial section view of the needle guard device through the lock collar tabs after the syringe sharp has been fully retracted from the injection site and the retention arms have resiled into place under the lock collar tabs to prevent the device shield from moving proximally and lock the needle guard device in a fully needle stick safe state.
Figure 23:
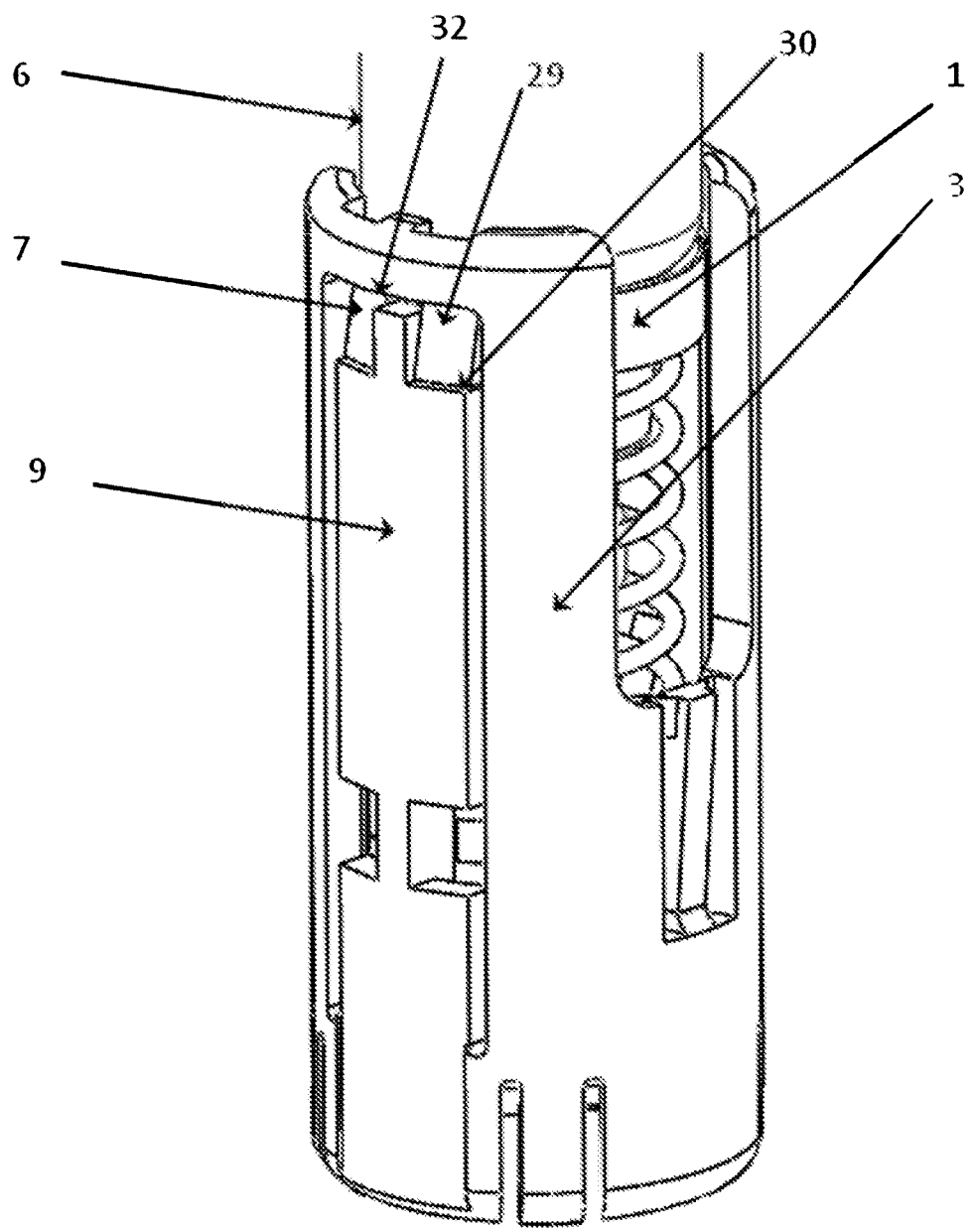
FIG. 23 is an isometric partial view of the needle guard device after the syringe sharp has been fully retracted from the injection site and the retention arms have resiled into place under the lock collar tabs to prevent the device shield from moving proximally.

When the retention arms 9 of the device shield 3 have been flexed radially outward as described above, the retention arm seat areas 27 lose contact with the top horizontal surface 26 of the lock collar tabs 7, and move into contact with an angled outer surface 28 of the lock collar tabs 7 as shown in FIG. 19. Consequently, once the user has finished their injection and begins to remove the syringe sharp (needle) 17 from the injection site 21, as shown in FIG. 20, the device shield 3, which is released from the lock collar 1 and biased by the spring 2 to move relative to the lock collar 1, travels distally from a first position toward a second position along the axis of the syringe 6, remaining in contact with the skin S around the injection site 21, and shielding the syringe sharp (needle) 17. Once the user has sufficiently removed the syringe sharp 17 from the injection site 21 and the syringe sharp 17 is completely shielded, but just prior to releasing the device shield 3 from contact with the skin S around the injection site 21, the device shield retention arms 9 snap into a locked position with the lock collar 1 as shown in FIGS. 21-23 to prevent proximal movement of the device shield 3 relative to the lock collar 1. At the proximal end of the device shield 3 are lock seat areas or cutouts 29 formed in the retention arms 9, which the lock collar tabs 7 fit within. As a result, at the end of the distally directed travels of the device shield 3, the retention arms 9 lose contact with the angled surface 28 of the lock collar tabs 7 and are free to resile into a vertical position where the top surface 30 of the lock seat area 29 of the retention arm 9 fits under the bottom surface 31 of the lock collar tab 7. Accordingly, if any contact occurred with the device shield 3 to push it proximally along the syringe 6, the device shield 3 would be prevented from moving proximally, protecting the user and others from an accidental needle stick injury. An upper surface 32 of the lock seat areas 29 of the device shield 3 contacts the top surface 33 of the lock collar tabs 7 and prevents the device shield 3 from being pulled distally off of the lock collar 1.

During needle 17 insertion and device activation, there are several contributors to the user force requirement for device activation. Not considering the force required for the needle 17 to be inserted into the patient, the forces potentially include, depending on the embodiment; the force required to bend or deflect the device shield retention arms 9, the force required to bend or deflect and activate the device shield feedback arms 22, and the force required to push the lock collar 1 proximally along the syringe neck 11. In the embodiment discussed above, in which the lock collar retaining arms 35 with lock collar pads 10 engage with the syringe bulbus 12 for retention of the needle guard device 13 to the syringe 6, the lock collar 1 must slide proximally along the syringe neck 11 upon insertion of the needle 17 in the patient in order to activate the needle guard device 13. Since the syringe neck 11 is tapered, being narrower near the bulbus 12 and larger near the barrel, the lock collar retaining arms 35 will need to flex during syringe insertion and device activation, adding to the force required to activate the needle guard device 13. It may be desirable to further reduce the syringe insertion and device activation force, which can be accomplished using the arrangement shown in FIGS. 24-25.

Figure 24:
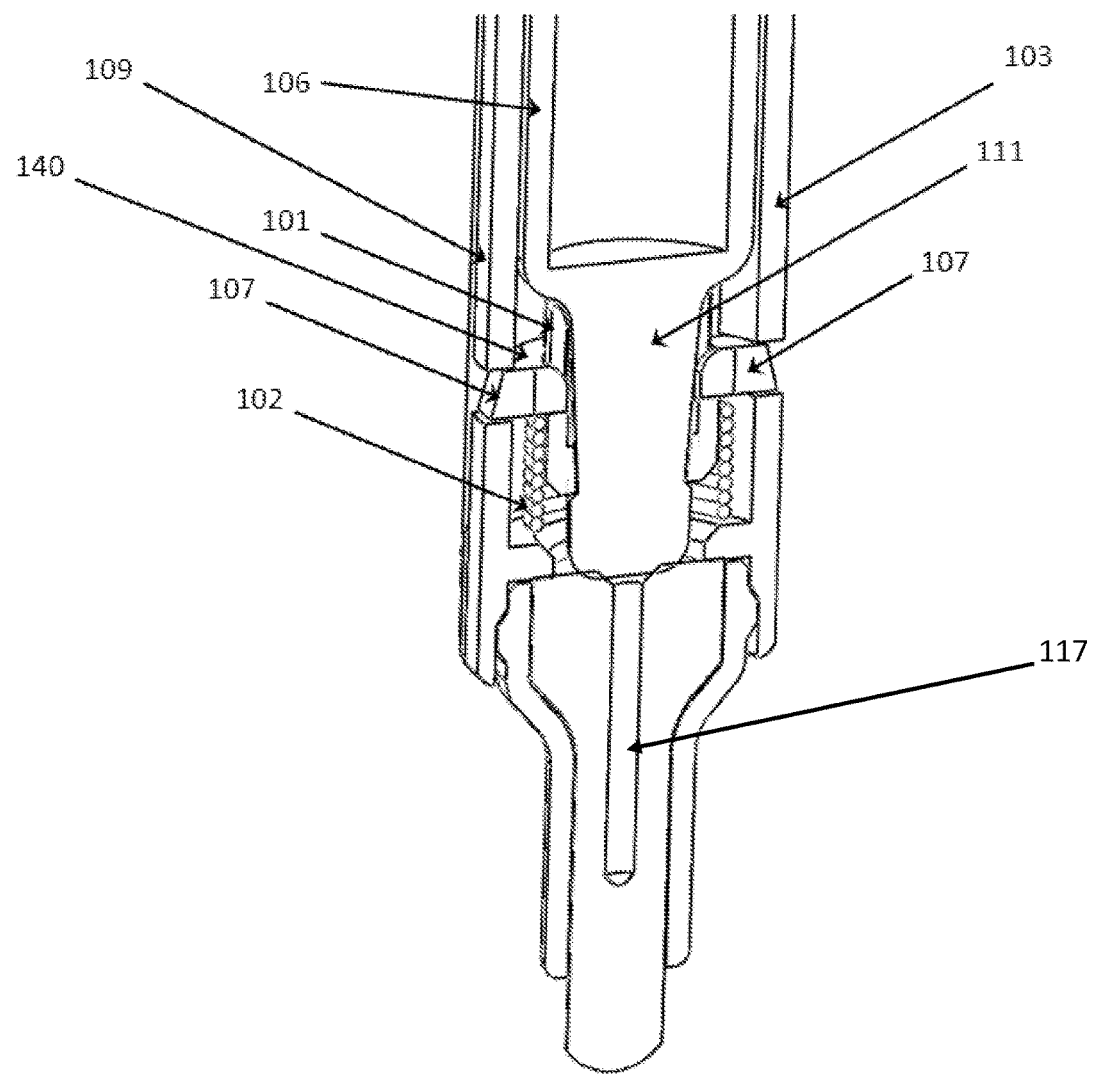
FIG. 24 is an isometric partial section view of an alternate embodiment of the needle guard device depicting a lock collar which remains fixed to the syringe neck and a lock collar ring containing the lock collar tabs that is freely slidable relative to the lock collar.
Figure 25:
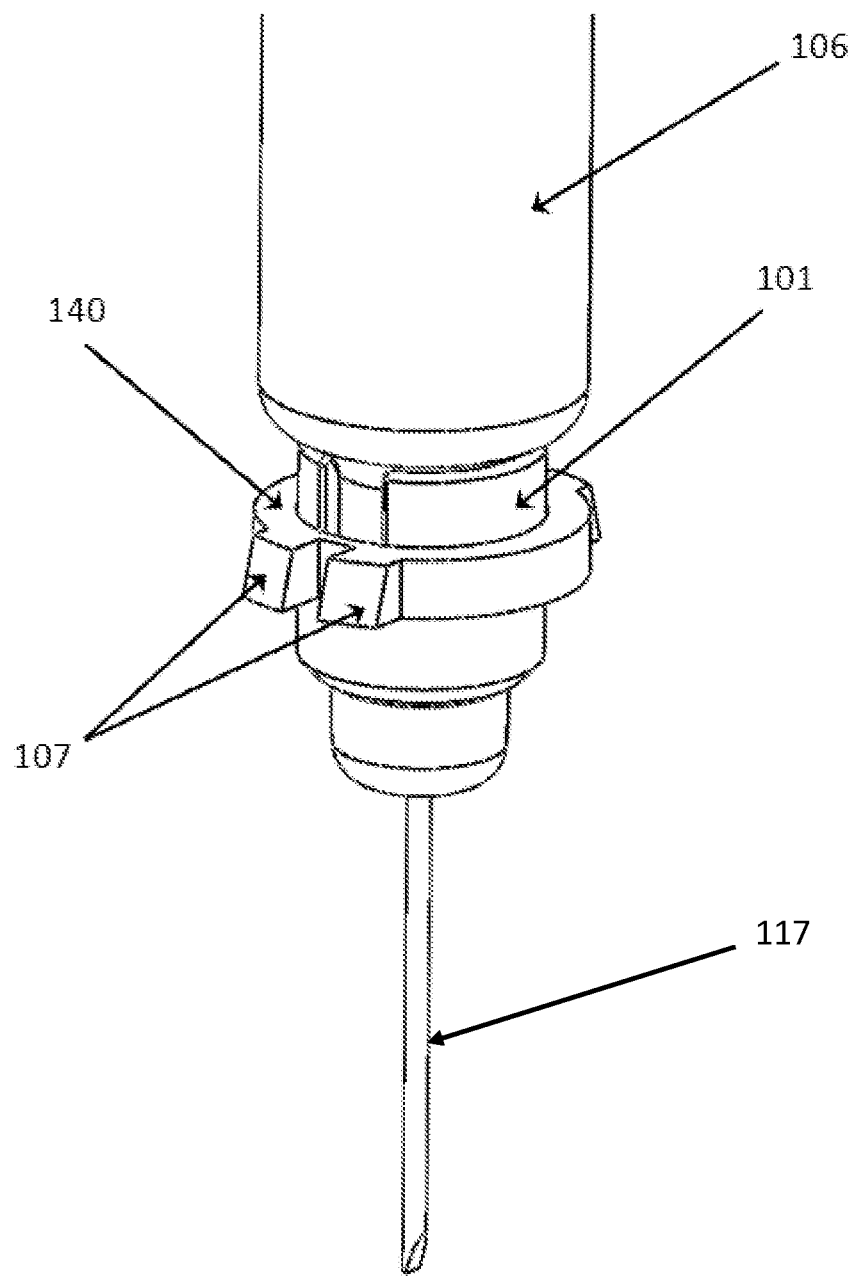
FIG. 25 is an isometric partial view of the syringe lock collar and lock collar ring assembled to a syringe.

In the embodiment depicted in FIGS. 24-25, a lock collar 101 is vertically fixed to the syringe 106 and lock collar tabs 107 are integrated into a lock collar ring 140 which can freely slide relative to the lock collar 101. In this embodiment, during syringe insertion and device activation, the lock collar ring 140 moves proximally with the device shield 103 until the device shield retention arms 109 flex or deflect enough radially to disengage with the lock collar ring tabs 107. At this point, the spring 102 would be free to push the device shield 103 over the syringe sharp 117. The lock collar 101 would remain fixed to the syringe neck 111 and not add to the force necessary to activate the safety device.

Figure 26:
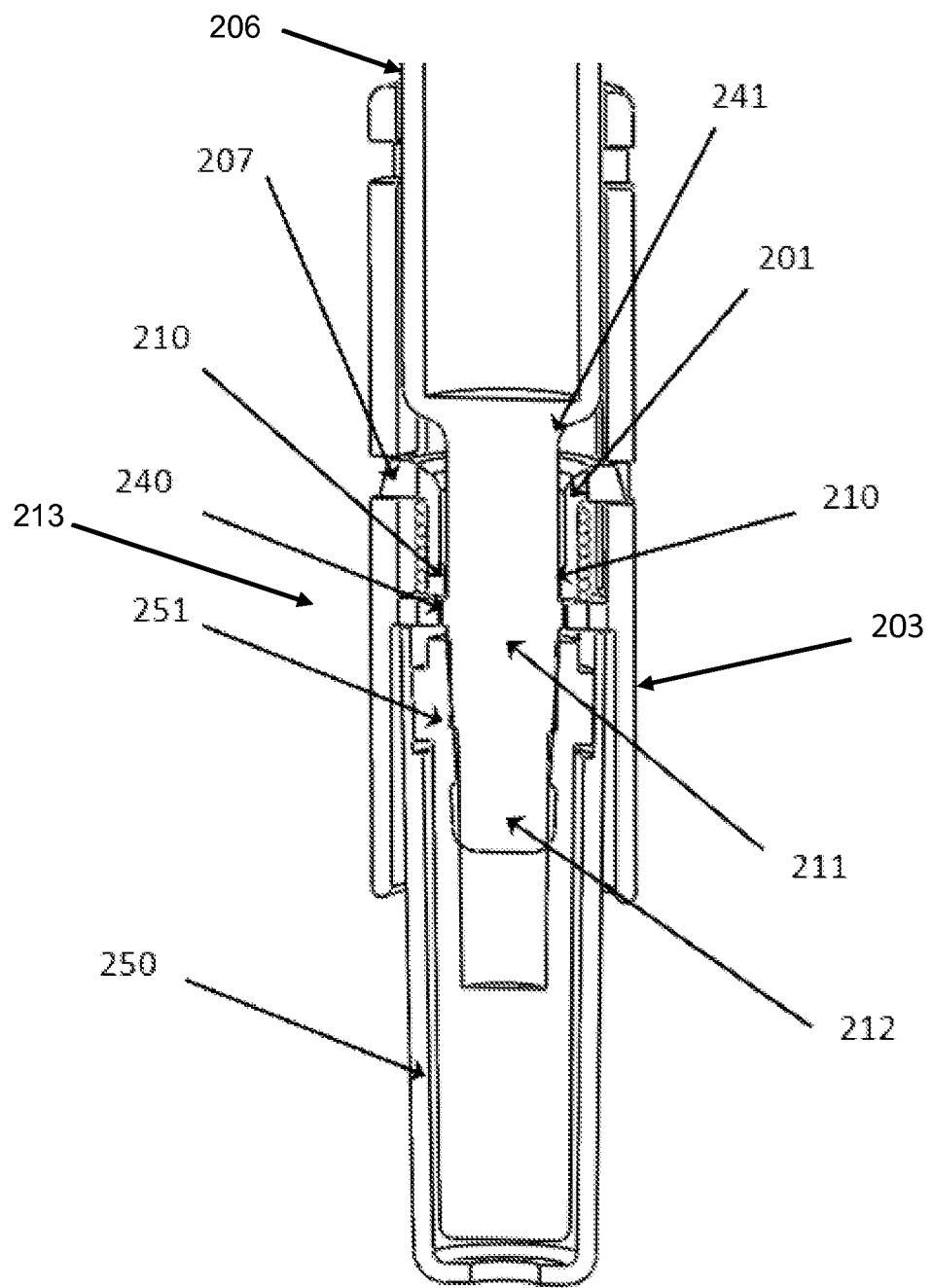
FIG. 26 is an isometric partial section view through lock collar tabs of an alternate rigid needle shield embodiment depicting a syringe with an elongated syringe neck, a rib on the syringe neck for retention of a lock collar, and a standard rigid needle shield.

In another embodiment shown in FIG. 26, a rigid needle shield may be used which may be considered a "standard" rigid needle shield, or one which is currently marketed and often used on glass, pre-filled syringes to protect the needle and drug, such as, e.g., the Stelmi rigid needle shield or the Becton Dickinson (BD) rigid needle shield. In this embodiment of a needle guard device 213, a lock collar 201 is attached to an elongated syringe neck 211 by means of a rib 240 on the syringe neck 211 and lock collar pads 210 located on the inner diameter of the lock collar 201. The inner diameter of the lock collar pads 210 is less than that of the outer diameter of the syringe neck rib 240. During assembly the lock collar 201 is forced over the syringe neck rib 240 thereby, retaining the lock collar between the syringe neck rib 240 and the syringe neck down area 241. An elastomeric portion 251 of a rigid needle shield 250 seals against a bulbus 212 of the syringe 206 as a standard rigid needle shield typically does. Additionally, the rigid needle shield 250 protrudes from the device shield 203, which is slidably coupled to the lock collar 201 sufficiently enough to allow a user to easily grab and remove it from the needle guard device 13.

Figure 27:
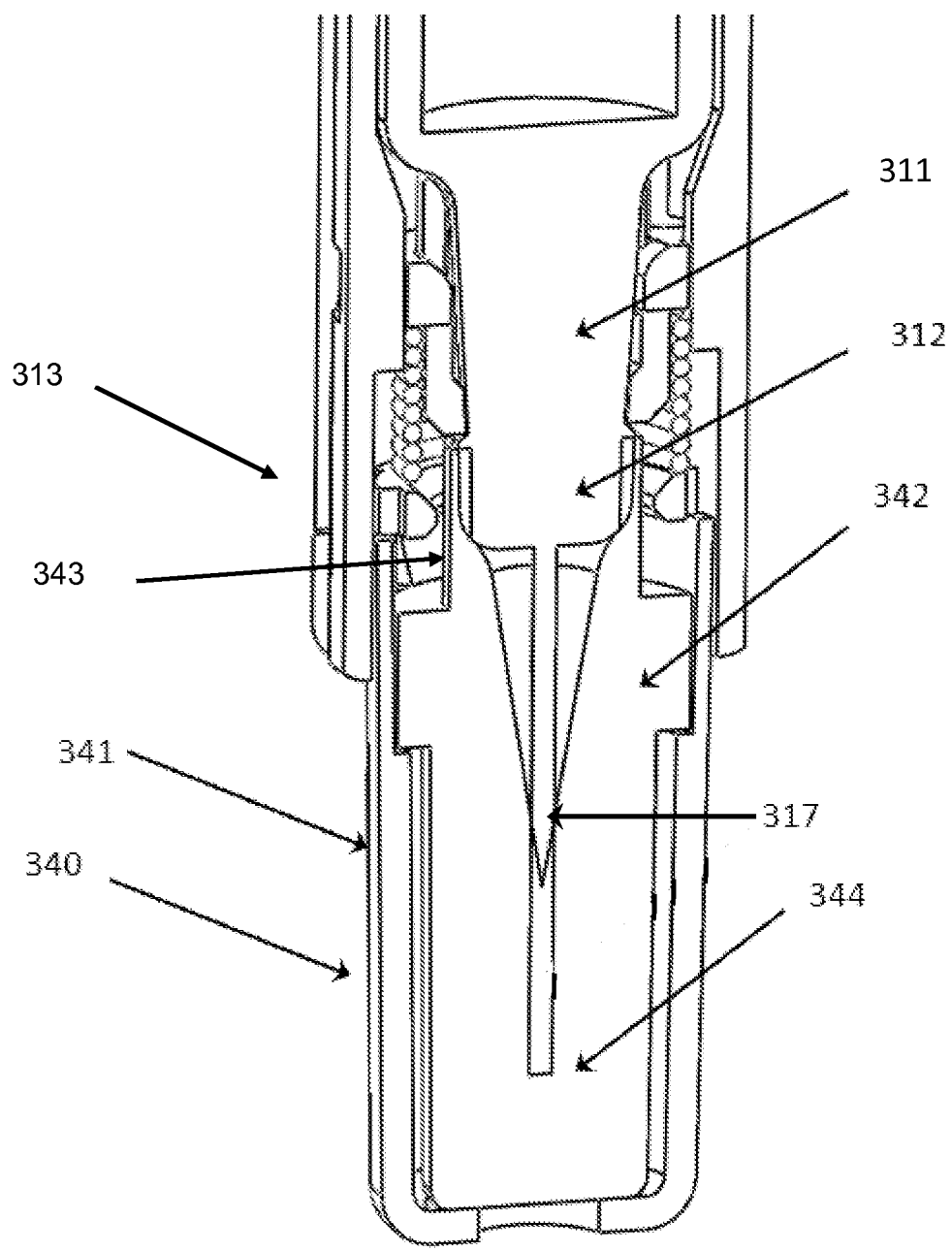
FIG. 27 is a section view of an alternate soft needle shield embodiment which creates a seal around the bulbus of the syringe rather than a gasket type seal against the bottom of the bulbus. The seal around the bulbus also acts to retain the rigid needle shield to the device by friction.

In another embodiment shown in FIG. 27, rigid needle shield 340, comprised of an outer thermoplastic 341 and an inner elastomer 342 is attached to the needle guard device 313 via friction between a neck 343 of the inner elastomer 342 and the syringe bulbus 312 of the syringe neck 311, and between a distal solid end 344 of the inner elastomer 342 and a syringe sharp 317. The friction interfaces described above also serve to protect the syringe sharp 317, create a seal between the syringe sharp 317 and the inner elastomer 342 to protect the drug from contaminants, and create a seal between the syringe bulbus 312 and inner elastomer 342 to protect the outer wall of the syringe sharp 317 from contaminants.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions shown in the process flow diagrams described herein is merely illustrative, unless otherwise stated, and the invention can be performed using different or additional process actions, or a different combination or ordering of process actions. As another example, each feature of one embodiment can be mixed and matched with other features shown in other embodiments. Features and processes known to those of ordinary skill may similarly be incorporated as desired. Additionally and obviously, features may be added or subtracted as desired. Accordingly, the invention is not to be restricted except in light of the attached claims and their equivalents.

What is claimed is:

1. A needle guard couplable to a syringe, the needle guard comprising
   a lock collar slideably couplable to a syringe; and
   a device shield transitionable from a first position in which a syringe sharp extends beyond the device shield to a second position in which the syringe sharp is covered by the device shield, the device shield comprising at least one radially deflectable retention arm,
   wherein, in the first position, the lock collar and the device shield are engaged to hold the device shield in the first position against the bias of a biasing member urging the device shield toward the second position, and movement of the syringe sharp relative to the device shield disengages the device shield from the lock collar enabling the device shield to transition to the second position, and
   wherein the lock collar includes at least one tab and the at least one retention arm engages the at least one tab to retain the device shield in the first position.

2. The needle guard of claim 1, wherein the biasing member is a spring positioned between the lock collar and the device shield.

3. The needle guard of claim 1, further comprising a needle shield assembly releasably coupled to the device shield, wherein the needle shield assembly is configured to prevent proximal movement of the device shield.

4. The needle guard of claim 1, wherein the at least one retention arm comprises at least one hole therethrough for receiving the at least one tab.

5. The needle guard of claim 1, wherein the at least one retention arm includes a rib that interacts with the syringe to radially deflect the at least one retention arm.

6. A needle guard couplable to a syringe, the needle guard comprising
   a lock collar slideably couplable to a syringe; and
   a device shield transitionable from a first position in which a syringe sharp extends beyond the device shield to a second position in which the syringe sharp is covered by the device shield, the device shield comprising at least one radially deflectable retention arm,
   wherein, in the first position, the lock collar and the device shield are engaged to hold the device shield in the first position against the bias of a biasing member urging the device shield toward the second position, and movement of the syringe sharp relative to the device shield disengages the device shield from the lock collar enabling the device shield to transition to the second position, and
   wherein the lock collar comprises at least one retaining arm having a pad that interfaces with the syringe and abuts a stop on the syringe to limit distal movement of the lock collar relative to the syringe.

7. A needle guard couplable to a syringe, the needle guard comprising
   a lock collar couplable to a syringe, the lock collar comprising at least one retaining arm with a pad at an end that interfaces with the syringe and abuts a stop provided on the syringe to limit distal movement of the lock collar with respect to the syringe; and
   a device shield transitionable from a first position in which a syringe sharp extends beyond the device shield to a second position in which the syringe sharp is covered by the device shield, wherein, in the first position, the lock collar and the device shield are engaged to hold the device shield in the first position against the bias of a biasing member urging the device shield toward the second position, and movement of the syringe relative to the device shield disengages the device shield from the lock collar enabling the device shield to transition to the second position.

8. The needle guard of claim 7, wherein the biasing member is a spring positioned between the lock collar and the device shield.

9. The needle guard of claim 7, further comprising a needle shield assembly releasably coupled to the device shield, wherein the needle shield assembly is configured to prevent proximal movement of the device shield.

10. The needle guard of claim 7, wherein the device shield includes at least one retention arm and the lock collar includes at least one tab, wherein the at least one retention arm engages the at least one tab to retain the device shield in the first position.

11. The needle guard of claim 10, wherein the at least one retention arm comprises at least one hole therethrough for receiving the at least one tab.

12. The needle guard of claim 7, wherein the at least one retention arm includes a rib that interacts with the syringe to radially deflect the at least one retention arm.

13. A syringe assembly comprising:
   a syringe including a body, a step down region at a distal end of the body and a neck extending from the step down region; and
   a needle guard comprising:
      a lock collar couplable to the neck of the syringe, and
      a device shield transitionable from a first position in which a syringe sharp extends beyond the device shield to a second position in which the syringe sharp is covered by the device shield, wherein the device shield comprises at least one chamfered rib,
   wherein, in the first position, the lock collar and the device shield are engaged to hold the device shield in the first position against the bias of a biasing member urging the device shield toward the second position, and movement of the syringe relative to the device shield causes the step down region of the syringe to engage the at least one chamfered rib thereby disengaging the device shield from the lock collar and enabling the device shield to transition to the second position.

14. The syringe assembly of claim 13, wherein the biasing member comprises a spring positioned between the lock collar and the device shield.

15. The syringe assembly of claim 13, further comprising a needle shield assembly releasably coupled to the device shield, wherein the needle shield assembly is configured to prevent proximal movement of the device shield.

16. The syringe assembly of claim 13, wherein the device shield includes at least one retention arm and the lock collar includes at least one tab, wherein the at least one retention arm engages the at least one tab to retain the device shield in the first position.

17. The syringe assembly of claim 16, at least one retention arm comprises at least one hole therethrough for receiving the at least one tab.

18. The syringe assembly of claim 13, wherein the lock collar comprises at least one retaining arm having a pad that interfaces with the syringe and abuts a stop on the syringe to limit distal movement of the lock collar relative to the syringe.

19. The syringe assembly of claim 13, wherein the engagement of the step down region of the syringe with the at least one chamfered rib causes the at least one retention arm to deflect in a radial direction.

\* \* \* \* \*